United States Patent
Wei et al.

(10) Patent No.: US 8,124,064 B2
(45) Date of Patent: Feb. 28, 2012

(54) IN-VITRO DEPOSITION EVALUATION METHOD FOR IDENTIFYING PERSONAL CARE COMPOSITIONS WHICH PROVIDE IMPROVED DEPOSITION OF BENEFIT AGENTS

(75) Inventors: Karl Shiqing Wei, Mason, OH (US); Qing Stella, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 148 days.

(21) Appl. No.: 12/511,034

(22) Filed: Jul. 28, 2009

(65) Prior Publication Data
US 2010/0221698 A1   Sep. 2, 2010

Related U.S. Application Data
(60) Provisional application No. 61/084,125, filed on Jul. 28, 2008.

(51) Int. Cl.
*A61K 31/74* (2006.01)
(52) U.S. Cl. ............... 424/78.03; 424/70.1; 514/18.8
(58) Field of Classification Search .................. None
See application file for complete search history.

(56) References Cited

U.S. PATENT DOCUMENTS
5,037,818 A   8/1991   Sime
(Continued)

FOREIGN PATENT DOCUMENTS
EP        0817608 B1   10/1996
(Continued)

OTHER PUBLICATIONS
International Search Report dated Apr. 6, 2010, PCT/IB2009/053283, 7 pages.

*Primary Examiner* — N. C. Yang
*Assistant Examiner* — Richard Moerschell

(57) ABSTRACT

The present invention relates to an in-vitro deposition evaluation method and an system for evaluating deposition of personal care compositions. The method comprises the steps of providing a microplate and at least one body that is capable of movement within the plurality of wells of the microplate. The method comprises the steps of providing a sample that comprises a personal care composition and depositing sufficient volume of sample to submerge a body within the wells of the microplate. The method comprises the steps of providing a skin mimic and contacting the skin mimic and the microplate such that the skin mimic is exposed to the sample and the body. The method comprises the steps of causing at least one body to move wherein a portion of the sample is transferred to the skin mimic and quantifying the amount of the sample that is transferred to the skin mimic.

18 Claims, 6 Drawing Sheets

U.S. PATENT DOCUMENTS

| | | | |
|---|---|---|---|
| 5,543,074 A | 8/1996 | Hague et al. | |
| 5,674,511 A | 10/1997 | Kacher et al. | |
| 5,688,752 A | 11/1997 | Turner | |
| 5,756,436 A | 5/1998 | Royce et al. | |
| 5,804,540 A | 9/1998 | Tsaur et al. | |
| 6,004,544 A | 12/1999 | Schrader et al. | |
| 6,126,954 A | 10/2000 | Tsaur | |
| 6,136,765 A | 10/2000 | Glenn, Jr. et al. | |
| 6,156,713 A | 12/2000 | Chopra et al. | |
| 6,255,264 B1 | 7/2001 | Fleurot et al. | |
| 6,348,188 B1 | 2/2002 | Eccleson et al. | |
| 6,383,999 B1 | 5/2002 | Coyle et al. | |
| 6,395,691 B1 | 5/2002 | Tsaur | |
| 6,439,036 B1 | 8/2002 | Mansky | |
| 6,506,369 B2 | 1/2003 | Ambler et al. | |
| 6,534,456 B2 | 3/2003 | Hayward et al. | |
| 6,569,438 B1 | 5/2003 | Banowski et al. | |
| 6,645,511 B2 | 11/2003 | Aronson et al. | |
| 6,759,376 B2 | 7/2004 | Zhang et al. | |
| 6,780,826 B2 | 8/2004 | Zhang et al. | |
| 6,821,379 B2 | 11/2004 | Datta et al. | |
| 6,841,201 B2 | 1/2005 | Shanov et al. | |
| 6,849,584 B2 | 2/2005 | Geary et al. | |
| 6,930,078 B2 | 8/2005 | Wells et al. | |
| 7,073,965 B2 | 7/2006 | Look et al. | |
| 7,202,199 B2 | 4/2007 | Shiloach et al. | |
| 7,208,168 B2 | 4/2007 | Fleissman et al. | |
| 2002/0012646 A1 | 1/2002 | Royce et al. | |
| 2002/0045941 A1* | 4/2002 | Ishikubo et al. | 623/15.12 |
| 2002/0155077 A1 | 10/2002 | Galante et al. | |
| 2003/0108507 A1 | 6/2003 | Clipson et al. | |
| 2003/0118078 A1 | 6/2003 | Carlson et al. | |
| 2004/0017728 A1* | 1/2004 | Becker et al. | 366/141 |
| 2004/0057920 A1 | 3/2004 | Focht et al. | |
| 2004/0157754 A1 | 8/2004 | Geary et al. | |
| 2004/0195519 A1* | 10/2004 | Refregier et al. | 250/372 |
| 2004/0223991 A1 | 11/2004 | Wei et al. | |
| 2004/0234467 A1 | 11/2004 | Ananthapadmanabhan et al. | |
| 2004/0234468 A1 | 11/2004 | Kerschner et al. | |
| 2004/0234470 A1 | 11/2004 | Zhang et al. | |
| 2004/0234558 A1 | 11/2004 | O'Connor et al. | |
| 2004/0235691 A1 | 11/2004 | Pham et al. | |
| 2004/0235693 A1 | 11/2004 | Wei et al. | |
| 2004/0248748 A1 | 12/2004 | Wei et al. | |
| 2005/0220735 A1 | 10/2005 | Tsaur et al. | |
| 2005/0220736 A1 | 10/2005 | Polonka et al. | |
| 2006/0079417 A1 | 4/2006 | Wagner et al. | |
| 2006/0182699 A1 | 8/2006 | Taylor et al. | |
| 2006/0252662 A1 | 11/2006 | Soffin et al. | |
| 2007/0020691 A1* | 1/2007 | Kanter et al. | 435/7.1 |
| 2007/0059263 A1 | 3/2007 | Taniguchi et al. | |
| 2007/0128255 A1 | 6/2007 | Belcher et al. | |
| 2007/0135319 A1 | 6/2007 | Wei et al. | |
| 2007/0167338 A1 | 7/2007 | McHugh et al. | |
| 2007/0259795 A1 | 11/2007 | Carnali et al. | |
| 2007/0288186 A1 | 12/2007 | Datta et al. | |
| 2010/0158830 A1 | 6/2010 | Wei et al. | |

FOREIGN PATENT DOCUMENTS

| | | | |
|---|---|---|---|
| WO | WO 9526710 A1 | 10/1995 | |

* cited by examiner

IN-VITRO DEPOSITION EVALUATION METHOD FOR IDENTIFYING PERSONAL CARE COMPOSITIONS WHICH PROVIDE IMPROVED DEPOSITION OF BENEFIT AGENTS

CROSS REFERENCE TO RELATED APPLICATION

This application claims the benefit of U.S. Provisional Application No. 61/084,125, filed Jul. 28, 2008.

FIELD OF THE INVENTION

The present invention relates to an in-vitro deposition evaluation method which identifies personal care compositions with improved deposition and produces accurate, reproducible results which correlate to the results of in vivo methods.

BACKGROUND OF THE INVENTION

Researchers in the beauty care industry are in a continuous search for new ingredients and new combinations of ingredients which improve the deposition of benefit agents from personal care compositions. Commonly, researchers use in vivo methods which utilize both human test subjects and human test administrators in the evaluation of deposition of personal care compositions. In using in vivo methods, skilled testing administrators have had to adopt rigid protocols and numerous human test subjects in order to make reliable predictions and evaluations of the deposition of benefit agents from personal care compositions. If administered rigidly, these in vivo methods provide the most accurate results due to the unique characteristics of human skin. In using in vivo methods, variations in administration of test protocols or in the skin characteristics of the human test subjects can lead to variability which impacts the results of the evaluation. Moreover, in vivo test methods can be expensive, laborious and time consuming. However, due to the unique characteristics of human skin, these in vivo methods are difficult to simulate and automate by in vitro methods which do not utilize human test subjects for evaluation. Thus, researchers have long sought an in-vitro test method for the evaluation of the deposition of benefit agents from personal care compositions which produce accurate, reproducible results which correlate to the results of in vivo methods.

SUMMARY OF THE INVENTION

In one embodiment, the present invention relates to an in-vitro deposition evaluation method. The method comprises the step of providing a microplate that comprises a base comprising a surface that comprises plurality of wells defined in the surface of the microplate. The method comprises the step of providing at least one body in each of said plurality of wells and each body is capable of movement within the well. The method comprises the step of providing a sample that comprises a personal care composition. The method comprises the step of depositing a volume of the sample into each of the plurality of wells sufficient to submerge at least one body. The method comprises the step of providing a skin mimic that comprises a treated test region. The method comprises the step of contacting the treated test region to the surface of the microplate such that the treated test region is exposed to the sample and the body within each of the plurality of wells. The method comprises the step of causing at least one body to move wherein a portion of the sample is transferred to the treated test region of the skin mimic. The method comprises the step of quantifying an amount of the sample that is transferred to the treated test region of the skin mimic.

In another embodiment, the present invention relates to an in-vitro deposition evaluation method. The method comprises the step providing a microplate that comprises a base that comprises a surface that comprises a plurality of wells defined in the surface. The method comprises the step of providing at least one body that comprises magnetic material in each of the plurality of wells; each body capable of movement within the well. The method comprises the step of providing a sample that comprises a personal care composition. The method comprises the step of depositing a volume of the sample into each of the plurality of wells sufficient to submerge at least one body. The method comprises the step of providing a skin mimic that comprises a treated test region comprising a plasma deposited 1,1,1-trimethyl-1-pentene coating. The method comprises the step of contacting the treated test region to the surface of the microplate such that the treated test region is exposed to the sample and the body within each of the plurality of wells. The method comprises the step of causing at least one body to move by the application of magnetic force wherein a portion of the sample is transferred to the treated test region of the skin mimic. The method comprises the step of quantifying an amount of the sample that is transferred to the treated test region of the skin mimic by spectroscopy.

In another embodiment, the present invention relates to system for evaluating in-vitro deposition. The system comprises at least one microplate that comprises a base that comprises a surface that comprises a plurality of wells defined in the surface. The system comprises at least one body in each of the plurality of wells and each body is capable of movement within the well. The system comprises at least one piece of skin mimic that comprises a treated test region; wherein the treated test region is in contact with the surface of the microplate such that the treated test region is exposed to the sample and the body within each of the plurality of wells. The system comprises a device for causing movement of at least one body to move wherein a portion of the sample is transferred to the treated test region of the skin mimic.

DETAILED DESCRIPTION OF THE INVENTION

Figure 1:
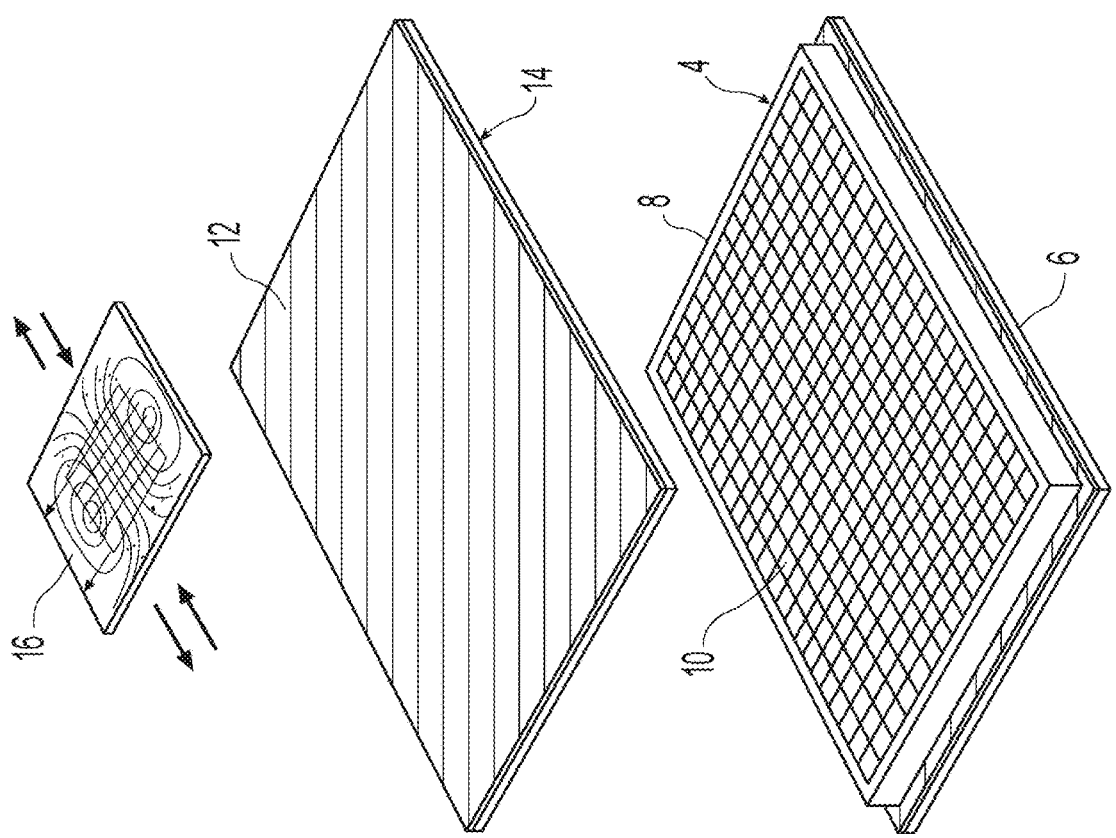
FIG. 1 is an exploded view of one embodiment of on embodiment of the system of the present invention.

The term "insoluble" as used herein, describes a property of a material or materials such that said material is incapable of being dissolved in the sample, a personal care composition, ingredients of a personal care composition and water.

The term "inert" as used herein, describes a property of a material or materials such that the material lacks any chemical, physical or biological action or reaction to any component of the sample, a personal care composition, ingredients of a personal care composition and water.

The term "multiphase" as used herein means that compositions comprise at least two phases which are chemically distinct (e.g. a surfactant phase and a benefit phase). These phases are in direct physical contact with one another and are not separated by a barrier. In some embodiments, the phases of the multiphase personal care composition are blended or mixed to a significant degree. In other embodiments, the phases of the multiphase personal care composition are made to occupy separate but distinct physical spaces inside the package in which they are stored, are not separated by a barrier and they are not emulsified or mixed to any significant degree. In one embodiment, the multi-phase personal care compositions comprise at least two visually distinct phases which are present within a container as a visually distinct pattern. The pattern results from the combination of the phases of the multiphase personal care composition by a method of manufacture herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, tessellated and mixtures thereof.

In one embodiment, the striped pattern can be relatively uniform across the dimension of the package. In another embodiment, the striped pattern is uneven (e.g. wavy), or non-uniform in dimension. The striped pattern does not extend across the entire dimension of the package in some embodiments. The stripe size is at least about 0.1 mm in width and 10 mm in length as measured from the exterior of the package in some embodiments. In another embodiment, the stripe size is about 1 mm in width and at least 20 mm in length as measured from the package exterior. In some embodiments, the phases are colored in order to offset its appearance from the other phase or phases present. In some embodiments, one phase contains particles, glitter or pearlescent agents in order to offset its appearance from the other phase or phases present.

The term "personal care composition" as used herein, refers to a composition that is formulated for topical application to the skin or hair. The personal care compositions are rinse-off personal care compositions that are formulated to be first applied topically to the skin and/or hair and subsequently rinsed off the skin and/or hair immediately, within minutes with water, or otherwise wiped off using a substrate or a device. In some embodiments, the personal care compositions are shaving creams that are formulated to be first applied topically to the skin for lubrication and subsequently taken off with a shaving razor or rinsing with water during the act of shaving. The personal care composition is extrudable or dispensible from a package and, in most embodiments, exhibit a viscosity of from about 1,500 centipoise (cP) to about 1,000,000 cP. The form of the personal care compositions, some embodiments are liquid, semi-liquid, cream, lotion or gel. The form of the personal care composition, in some embodiments, can be solid or granular. In some embodiments, the personal care compositions include shampoo, conditioning shampoo, body wash, moisturizing body wash, shower gels, bar soaps, skin cleansers, cleansing milks, hair and body wash, in shower body moisturizer, pet shampoo and shaving creams.

The in-vitro deposition evaluation method and system of the present invention provide an accurate and reproducible, high through-put quantification method and system for identifying personal care compositions which provide improved deposition of benefit agents on the skin surface. The present invention is an in vitro deposition evaluation method that has results which correlate to the results of in vivo deposition evaluation methods; however, the method of the present invention does not use human test subjects or human test administrators. The method of the present invention simulates the effects of full scale cleansing, bathing, and/or showering on the skin surface of human test subjects; but uses skin mimic surface materials. The method of the present invention only uses a small sample volume comprising a personal care composition, for example, in most embodiments the sample volume is less than 4 ml. The method of the present invention provides researchers the capability to evaluate a large number samples at low sample volumes thereby dramatically accelerating the development of new and improved personal care compositions with enhanced deposition of benefit agents.

The in-vitro deposition evaluation method comprises the step of providing a microplate that comprises a base comprising a surface that comprises plurality of wells defined in the surface of the microplate. The each of the plurality of wells are defined by holes on the surface of the microplate. The inner walls of the holes in the surface define the walls of the well. The microplate comprises a plurality of wells which comprise any number of wells of size or shape, arranged in any pattern or configuration. The microplates are comprised of a variety of materials. Microplates, in some embodiments are injection molded from polystyrene, polypropylene and cyclo-olefin. In other embodiments, microplates are vacuum formed from polycarbonate. Some embodiments of the microplate comprise the industry standard multi-well plate formats selected from 12-well, 24-well, 96-well, 384-well, 1536-well and 9600-well microplates. Other embodiments, comprise formats selected from include single well, two well, six well and twenty-four well and 6144 well microplates. The wells of the microplate comprise a well volume that comprises a volume ranging from tens of nanoliters to several milliliters. In some embodiments, the well volume is 4 ml. In other embodiments, the well volume is 320 µl. In other embodiments, the well volume is 160 µl. In other embodiments, the well volume is 14 µl.

Suitable 96-well microplates are commercially available from PerkinElmer and from VWR.com. For example, the SpectraPlate 96-MG from PerkinElmer has 8 rows and 12 columns with a well volume of 400 µl. The SpectraPlate 96-MG comprises the approximate dimensions of 14.6 mm in height, 127.8 mm in length and 85.5 mm in width. The SpectraPlate 96-MG has a well diameter of 7.15 mm, a well depth of 10.8 and a well to well spacing of 9.0 mm.

The in-vitro deposition evaluation method comprises the step of providing at least one body in each of the plurality of wells and each body is capable of movement within the well. The body within the container is a size and shape capable of moving within a well. The body has to be a size and a shape that allows movement of the body in multiple directions within the well. The body has to be a size and shape to fit into the container and be submerged within the sample. The body functions to move within the well such that wherein a portion of the sample is transferred to the treated test region of the skin mimic. The transfer of the sample to the skin mimic surface material is due to the repeated collision of the body and the skin mimic which simulates the effects of full scale cleansing, bathing, and/or showering on the skin surface of human test subjects. The type and amount of force the body applies to the skin mimic is dependent on size, shape, mass and surface texture of the body, as well as, the material that comprises the body.

In some embodiments, each of the plurality of wells can comprise a plurality of bodies. Each of the plurality of wells, in some embodiments, comprise from about 1 to about 9 bodies. Each body is made of a material which is insoluble and inert. The body, in most embodiments, is rigid but is sufficiently ductile to prevent breakage of the body upon collision with the walls of the wells or the skin mimic. In some embodiments, the body is flexible. The body has a smooth surface, in some embodiments. In other embodiments, the body has a rough surface. In some embodiments, the body is comprised of durable materials selected from metal, ferromagnetic material, magnetic material, ceramic, glass, enamel, concrete, rock, marble, gypsum, plastic, rubber, composites of the foregoing and combinations thereof. The body, in other embodiments, is made of a material that is coated with an insoluble, inert and ductile material. In some embodiments, the shape of the body comprises a shape selected from rectangular, spherical, round-flat, disk abate, cube shape, elongated cube shape, cylindrical shape, cylindrical rectangular shape, s-shaped and hexagonal shape. In some embodiments, container comprises 3 to 5 rectangular bodies that have the dimension of 3 mm by 1.6 mm by 1.9 mm. In other embodiments, sample comprises a plurality of bodies that are stainless steel spheres having diameter of less than 4 mm, less than 3 mm or less than 2 mm. One manufacture of bodies is WLB Antriebeselemente Gmbh, Scarrastrasse 12, D-68307 Mannheim, Germany.

The in-vitro deposition evaluation method comprises the step of providing a sample that comprises a personal care composition. In most embodiments, the personal care composition comprises both a surfactant component and a benefit component. In some embodiments, the personal care composition can be a multiphase lamellar composition, an isotropic composition or any type of emulsion known to one of ordinary skill in the art.

The surfactant component of a personal care composition comprises a mixture of lathering surfactants which are suitable for application to skin and hair and are compatible the other components of the personal care composition, including water. The personal care composition, in some embodiments, comprises from about 5% to about 30%, by weight of the personal care composition, of a mixture of lathering surfactants. In other embodiments, the personal care composition comprises from about 15% to about 22%, by weight of the personal care composition, of lathering surfactants. The lathering surfactants include anionic (e.g. sodium laureth sulfate, ammonium lauryl sulfate and sodium trideceth sulfate), nonionic (e.g. isosteareth-2, trideceth-3, TDA-3), cationic, zwitterionic (e.g. cocoamidopropyl betaine), amphoteric surfactants (e.g. sodium lauroamphoacetate, sodium cocoamphoactetate and disodium lauroamphoacetate) and mixtures thereof. Suitable surfactants for the multiphase personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The benefit component of the personal care composition comprises a mixture of hydrophobic moisturizing materials have a consistency value ranges of 10-1000 poise $(1/sec)^{n-1}$, a shear index range of 0.1-0.8 and Vaughan Solubility Parameter of from about 5 $(cal/cm^3)^{1/2}$ to about 15 $(cal/cm^3)^{1/2}$, as defined by C. D. Vaughan, *Solubility, Effects in Product, Package, Penetration and Preservation,* 103 Cosmetics & Toiletries, 47-69 (1988). In some embodiments, the benefit component is substantially free of water and substantially free of surfactants. The benefit component comprises from about 1% to about 99%, from about 3% to about 70%, from about 5% to about 60% and from about 10% to about 30%, by weight of the personal care composition, of hydrophobic moisturizing material. The hydrophobic moisturizing materials are selected from the group petrolatum, lanolin, derivatives of lanolin (e.g. lanolin oil, isopropyl lanolate, acetylated lanolin, acetylated lanolin alcohols, lanolin alcohol linoleate, lanolin alcohol riconoleate) hydrocarbon oils (e.g. mineral oil) natural and synthetic waxes (e.g. micro-crystalline waxes, paraffins, ozokerite, lanolin wax, lanolin alcohols, lanolin fatty acids, polyethylene, polybutene, polydecene, pentahydrosqualene) volatile or non-volatile organosiloxanes and their derivatives (e.g. dimethicones, cyclomethicones, alkyl siloxanes, polymethylsiloxanes, methylphenylpolysiloxanes), natural and synthetic triglycerides (e.g. castor oil, soy bean oil, sunflower seed oil, maleated soy bean oil, safflower oil, cotton seed oil, corn oil, walnut oil, peanut oil, olive oil, cod liver oil, almond oil, avocado oil, palm oil, sesame oil) and combinations thereof. The benefit phase of the personal care composition can be comprised a combination of petrolatum and mineral oil.

In some embodiments, the personal care compositions comprise less than about less than about 6%, less than about 5%, less than about 4%, less than about 3%, less than about 2%, less than about 1%, less than about 0.5%, less than about 0.25%, less than about 0.1%, less than about 0.01%, less than about 0.005%, by weight of the personal care composition, of the additional ingredients. Suitable optional ingredients comprised in some embodiments in either the surfactant component and/or the benefit component of personal care composition, are an optional ingredient selected from electrolytes, thickening agents, preservatives, antimicrobials, fragrances, chelators, such as those described in U.S. Pat. No. 5,487,884 (filed Oct. 22, 1982), sequestrants, density modifiers (e.g. low density modifiers comprising gas filled microspheres under the trade name EXPANDCEL® available from Akzo Nobel), lamellar phase inducing agents (e.g. electrolyte, non-ionic surfactant, fatty acids, ester derivatives, fatty alcohols, trihydroxystearin (e.g. THIXCIN® from Rheox, Inc.), cationic deposition polymers (e.g. JAGUAR® polymers from Rhodia, N-HANCE® polymers from Aqualon, R-30M, KG-30M, JR400 commercially available from Dow Chemical), non-ionic emulsifiers (e.g. glyceryl monooleate, glyceryl monooleate, glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, silicone copolyols), vitamins (e.g. Retinol), vitamin derivatives (e.g. tocophenyl actetate, niacinamide, panthenol), sunscreens, desquamation actives, such as those described in U.S. Pat. No. 5,681,852 (filed Jun. 7, 1995) and U.S. Pat. No. 5,652,228 (filed Nov. 12, 1993), anti-wrinkle/anti-atrophy actives (e.g. N-acetyl derivatives, thiols, hydroxyl acids, phenol), anti-oxidants (e.g. ascorbic acid derivatives, tocophenol), skin soothing agents/skin healing agents (e.g. panthenoic acid derivatives, aloe vera, allantoin), skin lightening agents (e.g. kojic acid, arbutin, ascorbic acid derivatives), skin tanning agents (e.g. dihydroxyacteone), anti-acne medicaments; essential oils, sensates; pigments; colorants; pearlescent agents; interference pigments, such as those disclosed in U.S. Pat. No. 6,395,691 (filed Feb. 28, 2001), U.S. Pat. No. 6,645,511 (filed Jan. 16, 2002), U.S. Pat. No. 6,759,376 (filed Sep. 11, 2002) and U.S. Pat. No. 6,780, 826 (filed Sep. 11, 2002) particles (e.g. talc, kolin, mica, smectite clay, cellulose powder, polysiloxane, silicas, carbonates, titanium dioxide, polyethylene beads), hydrophobically modified non-platelet particles described in Personal Care Compositions Containing Hydrophobically Modified Non-platelet particle, U.S. Patent Pub. No. 2006/0182699A (filed Feb. 15, 2005) (published on Aug. 17, 2006) and mixtures thereof. Such optional ingredients are most typically those materials approved for use in cosmetics and that are described in reference books such as the CTFA Cosmetic Ingredient Handbook, Second Edition (The Cosmetic, Toiletries, and Fragrance Association, Inc. 1988)(1992).

The in-vitro deposition evaluation method comprises the step of depositing a volume of the sample into each of the plurality of wells sufficient to submerge at least one body. The sample volume, in some embodiments, is less than 10 ml, is less than 2 ml and is less than 1 ml. In other embodiments, the sample volume is than less than 0.2 ml. In some embodiments, the sample volume is comparable to the well volume of commercially available microplates. Thus, in some embodiments, the sample volume is less than the container volume in a microplate. In some embodiments, the sample volumes is less than the container volume of a 24 well microplate, less than the container volume of a 96 well microplate, less than the container volume of a 384 well microplate, and less than the container volume of a 1536 well microplate. In other embodiments, the sample volume is a percentage of the volume of wells in a microplate. In these embodiments, the sample volume comprises from 5% to 95% of the container volume of a microplate. In other embodiments, the sample volume is less than 3.7 ml. In other embodiments, the sample volume is less than 320 µl. In other embodiments, the sample volume is less than 160 µl. In other embodiments, the sample volume is less than 14 µl. In one embodiment, sample comprises a personal care composition mixed with distilled water and transferred to the vessels in the 96 well microplate, the sample volume being less than the container volumes of the 96 well microplate.

In some embodiments, the method can comprise the step of preparing the sample. The sample can further comprise distilled water. The step of preparing the sample, in some embodiments, comprises diluting the sample. The step of preparing the sample, in some embodiments, comprises dispersing the sample. The step of preparing the sample, in some embodiments comprises adding distilled water at a ratio of distilled water to personal care composition. In some embodiments, the ratio of distilled water to personal care composition can range from 1:1 to 1:30. In other embodiments, the ratio of distilled water to personal care composition can range from 1:9 to 1:29. In other embodiments, the ratio of distilled water to personal care composition can range from 1:1 to 1:10. In other embodiments, the ratio of distilled water to personal care composition can range from 1:5 to 1:9. In other embodiments, the ratio of distilled water to personal care composition can range from 1:19 to 1:29. In some embodiments, the step of preparing the sample comprises the step of mixing the personal care composition with a solvent by a mixer at a speed of from about 300 rpm to about 700 rpm.

In other embodiments, the sample is not diluted or dispersed prior to being added to the wells. In these embodiments, the sample can be mixed within the wells of the microplate. When the sample is mixed within the wells of the microplate, the ratio of dilution is determined and then the amount of personal care composition and distilled water is added to the wells which comprise at least one body. The movement of the bodies within the wells mixes the samples.

The in-vitro deposition evaluation method comprises the step of providing a skin mimic that comprises a treated test region. The skin mimic are substrates that have properties of mammalian keratinous tissue. The coating material of the skin mimic surface material is stably affixed to the substrate to form a stable, coated surface which has a texture that mimics the topography of mammalian keratinous tissue, such as by the plasma deposition process described in U.S. Pat. No. 6,821,379 (filed Dec. 12, 2001) and U.S. Pat. No. 6,841,201 (filed Dec. 12, 2001). Further, the skin mimic surface materials demonstrate at least one physical property representative of mammalian keratinous tissue. The physical property representative of mammalian keratinous tissue is selected from the group consisting of a total surface energy, a dispersive component of the surface energy, a polar component of the total surface energy, a zeta-potential and combinations thereof. Comparison of properties of various skin mimics with human skin are shown in the examples below.

TABLE 1

Comparison of properties of various skin mimics with real skin

| Substrate | Surface Energy (mJ/m$^2$) | | | Zeta-Potential (mV) |
| --- | --- | --- | --- | --- |
| | Dispersive Component | Polar Component | Total | measured at a pH of about 5.0 |
| Normal Skin[2] | 30.30 | 0.20 | 30.50 | |
| Winter Skin[3] | 29.50 | 0.06 | 29.60 | |
| Summer Skin[4] | 29.70 | 3.10 | 32.80 | |
| Wet Skin[5] | 25.85 | 11.31 | 37.16 | |
| Scalp[6] | 29.30 | 12.70 | 42.00 | |
| Lips[7] | 33.00 | 5.50 | 38.50 | |
| Bicomponent polyurethane (TC-410)[8] | 47.31 | 2 | 49.31 | (−)22 |
| Polyurethane substrate with allyl amine coating layer | 32 ± 1.5 | 12 ± 1.5 | 45 ± 1.0 | (+)8.4 |

TABLE 1-continued

Comparison of properties of various skin mimics with real skin

| Substrate | Surface Energy (mJ/m²) | | | Zeta-Potential (mV) |
| --- | --- | --- | --- | --- |
| | Dispersive Component | Polar Component | Total | measured at a pH of about 5.0 |
| Polyurethane substrate with plasma deposited allyl alcohol coating layer | 28.9 | 12.6 | 41.45 | (−)7.1<br>(−)15.2 |
| Polyurethane substrate plasma deposited with 1,1,1-trimethyl-1-pentene coating layer | 31 ± 1 | 0.5 ± 0.3 | 32 ± 1.0 | (−)27.4 |
| Polyurethane substrate plasma deposited with PFMCH coating layer. | 19 ± 2.0 | 0.6 ± 0.2 | 20 ± 1.0 | (−)37.1 |
| VITRO SKIN (MS Inc., Orange, CT) | 31.55 | 8.52 | 40.07 | |
| COFFI film (Brechteen, Chesterfield, MI) | 28.06 | 9.12 | 37.17 | |
| BIOSKIN (Black) (Beaulax Co., Ltd., Tokyo, Japan) | 44.5 | 16.2 | 60.6 | |
| BIOSKIN (Brown) (Beaulax Co., Ltd., Tokyo, Japan) | 31.0 | 1.36 | 32.36 | |

Normal skin was measured from a human forearm. Measurements were made as follows: Shave any hair from skin 2-3 days prior to measurement. Place a drop of desired liquid on the skin, which is positioned horizontally. Capture the contact of the drip with a high speed (e.g. at 0.017 seconds per image) video stream for about 3 seconds. Use suitable software to non-spherically trace the droplets and determine the contact angle, e.g. First Ten Angstroms™ Model 200 Dynamic Contact Angle Analyzer. Calculate the mean contact angle for both sides of the drop. Scalp measurements and lip measurements were measured, as described for normal skin, except on the designated locations of the body.

Winter skin measurement were made as described for normal skin above at a temperature of approximately 0° C., a dew point of approximately −4° C. and a relative humidity of approximately 70%. Summer skin measurements were made as described for normal skin above at a temperature of approximately 24° C., a dew point of approximately 18° C. and a relative humidity of approximately 55%. Wet skin measurement made after immersion in distilled water for about 5 min. while still immersed. Solvents used to determine contact angles under water were bromonaphthalene, diiodomethane, and hexane. Contact angles converted into surface energy by Augustine Scientific, Cleveland, Ohio.

Suitable skin mimic surface materials are described in co-pending and co-assigned Coated substrate with properties of keratinous tissue, U.S Patent Pub. No. 20070128255A1 (filed Aug. 11, 2006) (published Jun. 7, 2007) and Methods of use of substrate having properties of keratinous tissue, U.S Patent Pub. No. 20070288186A1 (filed Feb. 5, 2007) (published Dec. 13, 2007).

Some embodiments, the step of providing the skin mimic comprises the steps of preparing the metallic mold (a), the step of forming the substrate of the skin mimic (b) and the step of forming the treated test mimic of the skin mimic.

The step of preparing the metallic mold comprises the step of making a pattern for the surface of the metallic mold. The pattern is made to resemble the surface of mammalian keratinous tissue, for example forearm skin, or hair. The step of creating the pattern is formed from computer-simulated images or an actual images (e.g. photographic, microscopic) of the human body part of interest. The step of preparing the metallic mold comprises the step of mechanically etching the pattern onto a metallic surface, following standard procedures of photolithography known to one of skill in the art. The preparation of the metallic mold, in some embodiments, comprises the step of transferring the pattern to a clear transfer sheet to form a mask. The preparation of the metallic mold, in some embodiments, comprises the step of adhering or laminating a photoresist to a metallic sheet that comprises copper, bass or other appropriate metal. A variety of photoresists are available commercially, for example DuPont™ MX series dry film photoresists. The selection of the photoresist is based on the desired size, texture and/or feature of the keratinous tissue-texture. The preparation of the metallic mold, in some embodiments, comprises the step of a placing the mask onto the metallic sheet to form a composite of metal/photoresist/mask. The preparation of the metallic mold, in some embodiments, comprises the step of exposing the composite of metal/photoresist/mask to an appropriate dose of UV light, using industry standard exposure tools. The preparation of the metallic mold, in some embodiments, comprises the steps of removing the mask and developing the photoresist. The preparation of the metallic mold, in some embodiments, comprises the step of etching the metal sheet using appropriate etching solutions, as described in standard textbooks on second level microelectronics packaging. For example, Donald Seraphim, Ronald Lasky and Che-Yu Li, Principles of Electronic Packaging (Mc-Graw Hill Inc.) (1989).

The step of forming the substrate of the skin mimic, in some embodiments, comprises selecting a substrate selected from polymers, glass, metal, fabric or combinations thereof. The step of forming the substrate, in some embodiments, comprises selecting and mixing a bicomponent polymer. In some embodiments, the polymer selected is a 1:1 mixture of Skin-Flex SC-89 Stretch-paint, available from Burman Industries (Van Nuys, Calif.) and Skin-Flex SC-89 Thinner S4 SC-89 Thinner, available from Burman Industries, (Van Nuys, Calif.). In some embodiments, the step of forming the substrate of the skin mimic, comprises the step of coloring the substrate such that deposition is measured with greater ease in the quantification step. The suitable colorant is chosen by one killed in the art to be compatible with both the substrate and the coating on the substrate if present. In some embodiments, the skin mimic is colored a dark shade such as black, brown, navy blue, violet or crimson. In other embodiments, the skin mimic is colored to comprise a variety of flesh tones.

The step of forming the treated test region of skin mimic in some embodiments, comprises the step of imparting skin surface properties by surface-modification and/or fixedly coating the skin mimic. Imparting skin surface properties, in some embodiments, comprises the step of coating the treated test region of the skin mimic by plasma deposition. The step of plasma deposition, in some embodiments, occurs in a plasma unit, between the two electrodes, by application of the RF power. The effective plasma treatment area is approximately 40 cm by 20 cm. The plasma unit comprises a cylindrical vacuum chamber having a diameter of approximately 30.5 cm and a length of 61.0 cm. In some embodiments, the vacuum is produced by means of a Leybold PCS 25 vacuum pump. The RF energy, in some embodiments, is supplied from a PE 1000 Advanced Energy 40 KHz power supply, across a set of parallel Al-electrodes in the vacuum chamber.

The skin mimic, in some embodiments, is polar having a surface energy of 1-8 $mJ/m^2$. The skin mimic, in other embodiments, is non-polar having a surface energy of 15-40 $mJ/m^2$.

In some embodiments, skin mimic is stabilized at room temperature ranging from about 20° C. to about 25° C. In other embodiments, skin mimic is stabilized at a typical shower temperature ranging from about 38° C. to about 39° C.

The skin mimic used in the exemplary embodiments of the in-vitro deposition methods is comprised of a molded bicomponent polyethylene substrate. The skin mimic is textured on one side with a pattern that resembles the texture of human skin. The textured side of the skin mimic is coated with 1,1,1-trimethyl-1-pentene that is plasma deposited using continuous wave deposition at 25W and 40 Khz power. The skin mimic has a total surface energy of 32±1.0 ($mJ/m^2$), a zeta potential of (−) 27.4 (mV), a contact angle in water of 100°±2.0.

The in-vitro deposition evaluation method comprises the step of contacting the treated test region to the surface of the microplate such that the treated test region is exposed to the sample and the body within each of the plurality of wells. The treated test region of the skin mimic covers the plurality of wells and acts as a lid for the microplate. The treated test region of the skin mimic contacts the surface of the microplate in such a way that a seal is formed between the openings of the plurality of wells and the skin mimic, so as to comprise no cross contamination between each of the plurality of wells.

The in-vitro deposition evaluation method comprises the step of causing at least one body to move wherein a portion of the sample is transferred to the treated test region of the skin mimic. The repeated movement or collision between the sample, the body and the skin mimic causes the transfer and deposition of the sample onto the treated test region of the skin mimic. In some embodiments, the movement of the body can be caused by an application of force to the body. In other embodiments, the movement of the body can be caused by an application of force to the sample, the body, the skin mimic, microplate and mixtures thereof.

The application of force, in some embodiments, is applied externally to the sample, the body, the skin mimic, microplate and mixtures thereof. The application of force, in other embodiments, is applied internally the sample, the body, the skin mimic, microplate and mixtures thereof. In some embodiments, force applied is a mechanical force, a magnetic force, an electromagnetic force, an electrostatic force, an electric force or mixtures thereof. In some embodiments, the mechanical force is applied by a device, such as by a microplate shaker. A suitable commercially available microplate shaker is VWR™ Signature High-Speed Microplate Shaker which is designed to shake and/or vortex microplates in timed or continuous modes at programmable speed from 600 to 2500 rpm (±25 rpm), and programmable timed mode from 1 to 9999 seconds (166 minutes). In other embodiments, the mechanical force applied is applied by a device such as a sonilator.

In some embodiments, the force that is applied is a magnetic, electromagnetic or electrostatic force that acts on force fields on magnetic materials. In some embodiments, the force is applied by a device such as the automated cleansing unit shown in FIG. 2, FIG. 3 and FIG. 4. Magnetic, electromagnetic and electrostatic forces act over distances penetrating non-susceptible materials including glass, plastic and non-ferromagnetic metals, to act on magnetic materials. In some embodiments, the bodies are comprised of a magnetic material. Each of the bodies are submerged within the samples contained within the plurality of wells of a microplate. In such an embodiment, the bodies are subjected to a magnetic force by a moveable magnet which moves relative to the microplate and the skin mimic. In such an embodiment, the magnetic field from the movable magnet causes the bodies to move within the sample and transfer the sample onto the treated test region of the skin mimic.

The force is applied with a measurable duration, frequency and amplitude. In some embodiments, the force is applied in a short duration and in other embodiments, the force is applied in a long duration. The force, in some embodiments, is applied in a continuous manner. In other embodiments, the force is applied in a discontinuous manner. The force, in some embodiments, is applied the force in a periodic manner. The force, in some embodiments, is applied directionally to the sample, the body, the skin mimic, the microplate and mixtures thereof. In some embodiments, the force is applied in an oscillating manner to the sample, the body, the skin mimic, microplate and mixtures thereof.

The method comprises a quantification step. The quantification step measures the amount of sample that is transferred to the treated test region of the skin mimic. The quantification step comprises analytical methods selected the general a category of spectroscopy, gravimetry, mass spectrometry, spectrophotometry, colorimetry, extraction, chromatography, electrophoresis and combinations thereof. In some embodiments, the skin mimic surface material is analyzed by reflectance of light with suitable reflectometers or calorimeters for the deposition of benefit agents from the personal care composition comprised in the sample applied to the skin mimic. The spectroscopy methods are selected from absorption, fluorescence, X-ray, X-ray fluorescence, flame, visible, ultraviolet, Raman, nuclear magnetic resonance and photoemission. In some embodiments, the spectroscopy method is Infared spectroscopy utilizing a Fourier Transfer Infared Spectrophotometer (herein after known as "FTIR"). The deposition of the samples of Examples 1 to 5 was quantified utilizing an Eye-One® IO Spectrophotometer to measure the L-a-b values. In some embodiments, the optical methods are coupled with reactions to staining compounds and indicators. In some embodiments, the chromatography is selected from column chromatography, liquid chromatography and gas chromatography. In example 7, described below the quantification step was performed by high performance liquid chromatography (hereinafter referred to as "HPLC") and gas chromatography (hereinafter referred to as "GC"). In other embodiments, physical measurements are the measurements of the changes in the known properties of the skin mimic surface material. In some embodiments, the quantification step comprises calculating a change in the known physical measurements of the skin mimic such as, changes in zeta potential, changes in surface energy, changes in polarity and combination thereof. In some embodiments, the quantification step is performed by an Enzyme-Linked ImmunoSorbent Assay, also called ELISA, to detect the presence of an antibody or an antigen in the sample.

The advantage of speed and capacity of in evaluating the deposition of personal care compositions relies, at least in part, on the system for evaluating the in-vitro deposition of a personal care composition.

FIG. 1 is an exploded view of one embodiment of a system 2 of the present invention. The system 2 comprises at least one microplate 4 that comprises a base 6 that comprises a surface 8 that comprises a plurality of wells 10 defined in the surface 8. The system 2 comprises at least one body (not shown) in each of the plurality of wells 10 and each body is capable of movement within the well 10. The system also comprises at least one piece of skin mimic 12 that comprises a treated test region 14; wherein the treated test region 14 is in contact with the surface 8 of the microplate 4 such that the treated test region 14 is exposed to the sample, as described above, and the body within each of the plurality of wells 10.

The system 2 comprises a device 16 for causing at least one body to move wherein a portion of the sample is transferred to the treated test region 14 of the skin mimic 12. The device 16, in most embodiments, causes repeated collision between the sample, the body and the skin mimic 12, which causes the transfer and deposition of the sample onto the skin mimic 12. The device 16 can be any device one of ordinary skill can envision that would cause at least one body to move wherein a portion of the sample is transferred to the treated test region 14 of the skin mimic 12. The device 16, in some embodiments, causes the movement of body within each of the plurality of wells 10 by an application of force to the body. However, in other embodiments, the device 16 causes the movement of body within each of the plurality of wells 10 by an application of force to the sample, the body, the skin mimic 12, microplate 4 and mixtures thereof. The device 16, in some embodiments, applies a mechanical force, a magnetic force, an electromagnetic force, an electrostatic force, an electric force or mixtures thereof. In some embodiments, the device 16 is a device that applies a mechanical force such as by a microplate shaker. A suitable commercially available microplate shaker is VWR™ Signature High-Speed Microplate Shaker which is designed to shake and/or vortex microplates in timed or continuous modes at programmable speed from 600 to 2500 rpm (±25 rpm), and programmable timed mode from 1 to 9999 seconds (166 minutes). In some embodiments, the device 16 applies a magnetic, electromagnetic or electrostatic force that acts on force fields on magnetic materials, such as the automated cleansing unit shown in FIG. 2, FIG. 3 and FIG. 4. The device 16, in some embodiments, applies a force externally to the sample, the body, the skin mimic 12, microplate 4 and mixtures thereof. The device 16 applies a force with a measurable duration, frequency and amplitude. The device 16 applies a force, in some embodiments, of a short duration and in other embodiments in a long duration.

The device, in some embodiments, applies a force in a continuous manner. In other embodiments, the device 16 applies a force is a discontinuous manner. The device 16, in some embodiments, applies the force in a periodic manner. The device 16, in some embodiments, applies force directionally to the sample, the body, the skin mimic 12, microplate 4 and mixtures thereof. In some embodiments, the device 16 applies force in an oscillating manner to the sample, the body, the skin mimic 12, microplate 4 and mixtures thereof.

Figure 2:
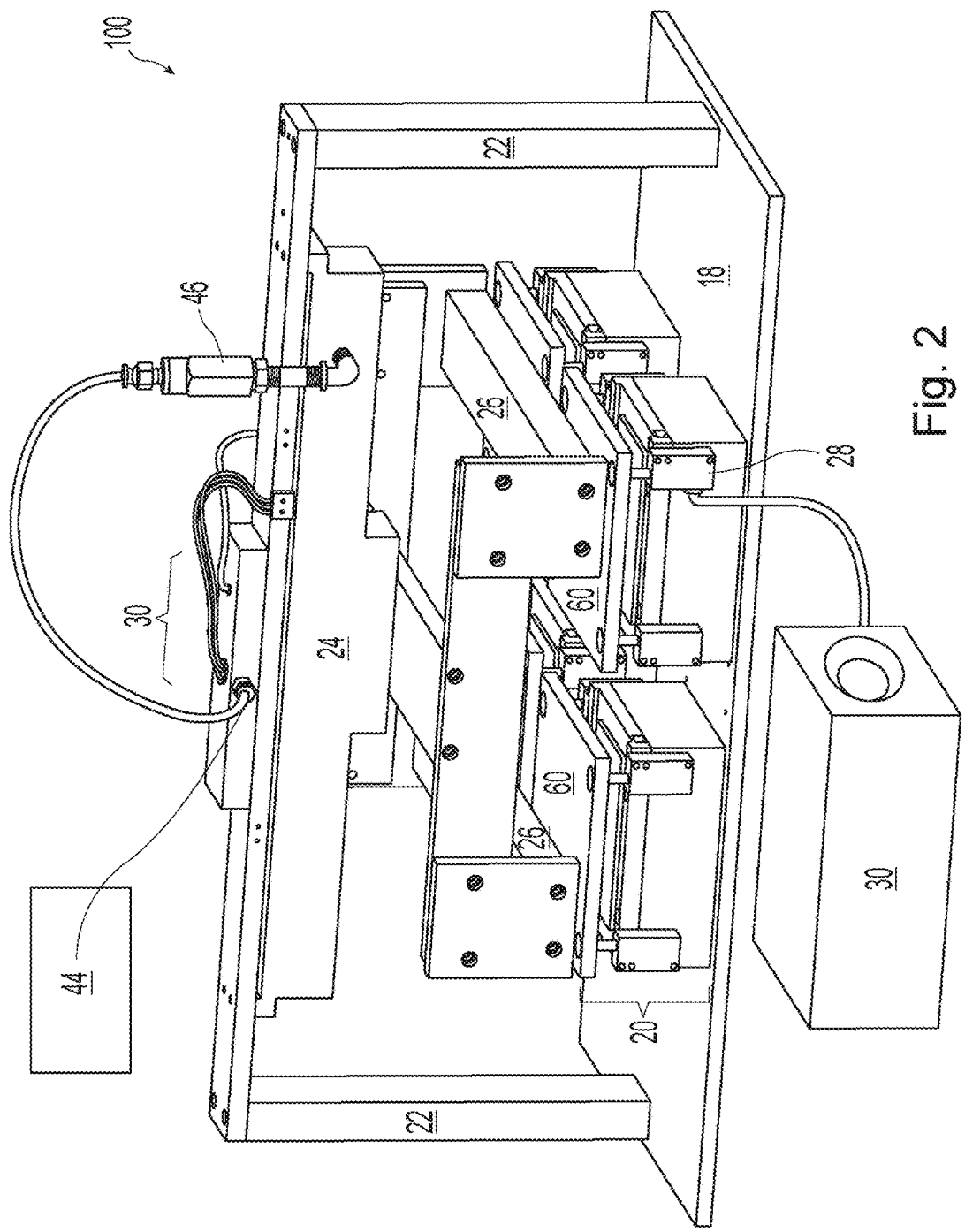
FIG. 2 is an isometric view of one embodiment of an automated cleansing unit, device used in the exemplary embodiment of the in vitro deposition method of the present invention.

FIG. 2 is an isometric view of one embodiment of an automated cleansing unit 100, a device used in an exemplary embodiment of the in vitro method of the present invention. The automated cleansing unit 100 is comprises a horizontal base 18 comprising four microplate holders 20. The horizontal base 18 is made of various materials, for example, aluminum. In some embodiments, the horizontal base is and comprises the following approximate dimensions of ⅜ inch in height, fourteen inches in width and twenty seven inches in length. The automated cleansing unit 100 comprises two vertical supports 22. The two vertical supports 22, in some embodiments, are comprised of aluminum. The two vertical supports comprise the approximate dimensions of one inch by two inches by ten and ¾ of an inch in height. The vertical supports 22 are attached to a horizontal support comprising a rodless air slide 24. In some embodiments, horizontal support comprising a rodless air slide 24 comprises the approximately dimension of a ½ inch by two inches by twenty six and ½ inches in height. The automated cleansing unit 100 comprises two magnetic arms 26. The horizontal support comprising a rodless air slide 24 is the structure upon which the two magnetic arms 26 are mounted. The rodless air slide 24 comprises a carriage that is connected to an internal piston (not shown). The rodless air slide 24 is double acting with two compressed air port (not shown): one to extend in the "push" direction and another to retract in the "pull" direction. Suitable rodless air slides 24 with a one inch bore and eleven inch stroke, associated end lugs and mount brackets are commercially available from McMaster-Carr®. The rodless air slide 24 is connected to the pneumatic control unit 30.

The magnetic arms 26 are mounted to the rodless air slide 24 such that the magnetic arms 26 move back and forth along the length of the double acting rodless air slide 24 by the force of compressed air. Each of the magnetic arms 26 are comprised of aluminum. The magnetic arms 26 have the dimensions of one inch by two inches by fourteen inches in length and have a "T" shape channel that houses seven neodymium iron boron magnets (not shown). Each of the neodymium iron boron magnets, in some embodiments, are sized having the approximate dimensions of two inches in length, one inch in width and half or an inch in height. Each of the neodymium iron boron magnets, in some embodiments, comprises a magnetic strength of 12200 Gauss. Suitable neodymium iron boron magnets are available from Edmund Scientifics. The magnetic arms 26 are configured at a height above the microplate holder 20 which is adjustable with the caveat that the magnets at the height chosen must maintain their function to attract and move the bodies comprised within the wells of the microplate. In some embodiments, the magnetic arms 26 are configured at a height above the microplate holder 20 that ranges approximately from about 2.50 cm to about 3.00 cm above the microplate holder 20. In some embodiments, the magnetic arms 26 are configured at a height above the microplate holder 20 that ranges approximately from about 2.75 cm above the microplate holder 20. The magnetic arms 26 move back and forth along the length of the rodless air slide 24 by the force of compressed air at an adjustable speed. In some embodiments, the speed of the magnetic arms 26 is approximately six back and for the sweeps over the length of the rodless air slide 24 over a 10 second time period.

Below the magnetic arms 26 are configured four microplate holders 20. Each of the microplate holders 20 comprise a clamping plate 60 and four pistons 28 attached to a pneumatic control unit 30. When actuated, the pistons 28 for the pneumatic control unit 30 hold the microplates in the four microplate holders 20 at a pressure of from about 80 to around 100 psi. In some embodiments, the pistons 28 for the pneumatic control unit 30 when actuated hold the four microplates in the microplate holders 20 at a pressure of 90 psi.

Figure 3:
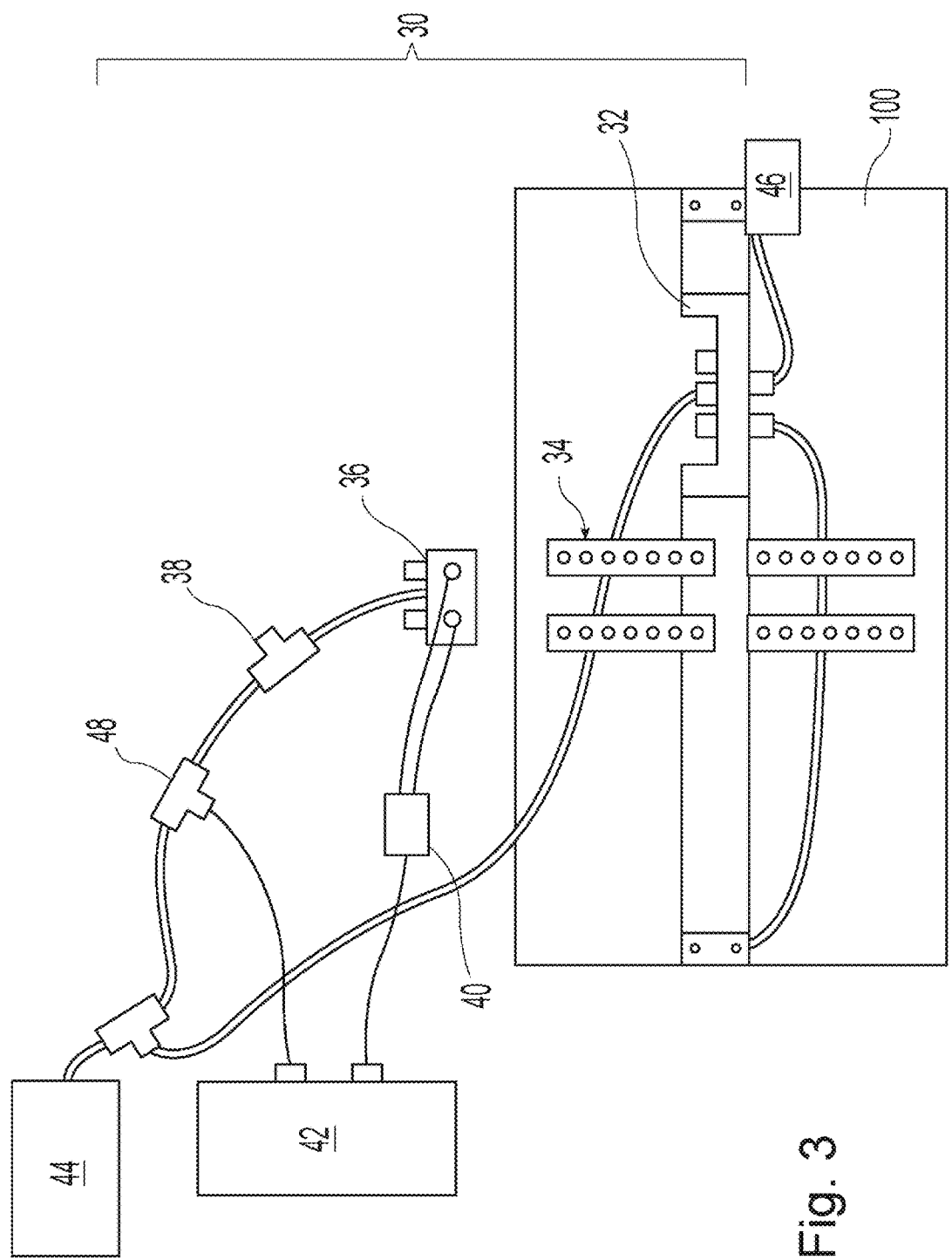
FIG. 3 is a top view of the automated cleansing unit comprising one embodiment of the pneumatic control unit used in the exemplary embodiment of the in vitro deposition method of the present invention.

FIG. 3 is a top view of the automated cleansing unit 100 comprising one embodiment of the pneumatic control unit 30. The top view shows components of the pneumatic control unit 30 which are connected to the rodless air slide 24, the piston 28 and clamping plates 60 shown in FIG. 2. The pneumatic control unit 30 is used to apply compressed air to the automated cleansing unit 100, which imparts a force by converting the potential energy of compressed air into kinetic energy. The pneumatic control unit 30 comprises a solenoid air control valve 32, a distribution manifold outlet 34, a compressed air control valve 36, a compressed air flow regulator 38, an alternating output binary valve 40, a two-hand safety pneumatic control valve 42, a compressed air control valve 46 and various connectors 48 that provide pressurized air to the automated cleansing unit 100 from an external air source 44. The air control valve 36, air flow regulators 38, alternating a binary valves 40, a two-hand safety pneumatic control valve 42 are positioned upstream of a solenoid air control valve 32. A suitable solenoid air control valve, in one embodiment, is described as a double air style valve with a 10 psi to 120 operating pressure. Suitable compressed air flow regulators 38, in some embodiments, operate in the pressure range of 14 psi to 116 psi. Suitable air control valve alternating output binary valves 40, in some embodiments, operate in a 35 psi to 100 psi range. All of the components of the pneumatic control unit 30 are available from McMaster-Carr®. It is to be understood that the pneumatic control unit 30 shown in FIG. 3 and the operation described herein are one embodiment which supply compressed air to the automated cleansing unit. One of ordinary skill in the art will readily appreciate that other systems may be used to compressed air to the automated cleansing unit 100.

Figure 4:
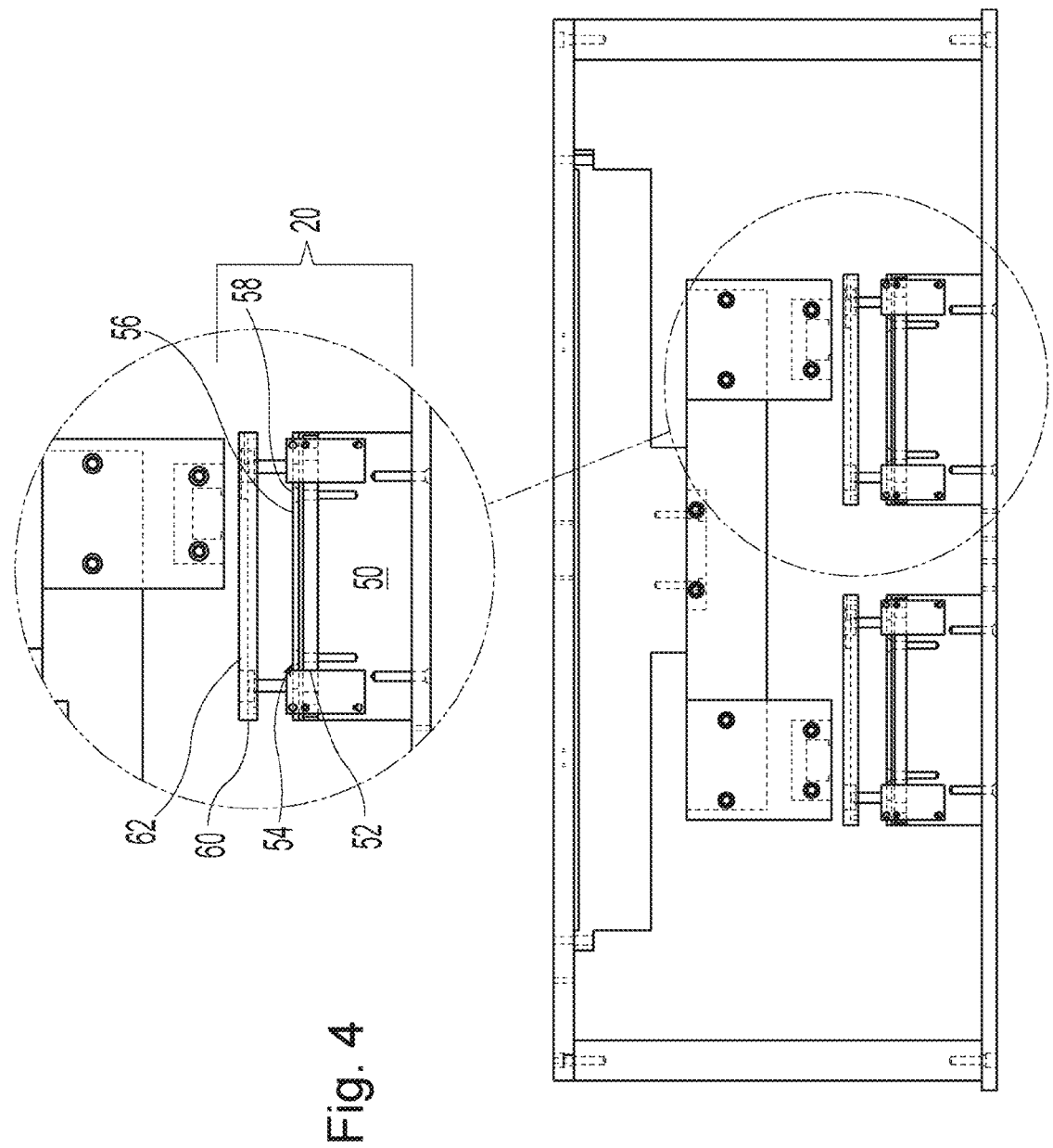
FIG. 4 is a detailed cut away side view of one of the microplate holder 20 of the automated cleansing unit 100, used in the exemplary embodiment of the in vitro deposition method of the present invention.

A detailed cut away side view of the microplate holder 20 is shown in FIG. 4. The microplate holder 20, in one embodiment, is designed to hold four commercially available 96 well microplates. The microplate holder 20 comprises a riser 50, an aluminum base plate 54, a clamping plate 60 and pistons 28. Riser 50 has a larger dimension than the approximately dimension of a commercially available microplate. In some embodiments, the riser 50 has the dimensions of inches by five inches by five and ¾ inches. The riser 50 is comprised of polyoxymethylene which is commonly known under DuPont's brand name DELRIN®. DELRIN® is used as a metal substitute because it is a lightweight, low-friction, and wear-resistant thermoplastic that possesses good physical and processing properties and capable of operating in temperatures in excess of 90° C. In addition to the riser 50, the microplate holder, in some embodiments, comprises an aluminum base plate 54. The aluminum base plate 54 has a raised portion 56 and a trench 58 which is approximately the same dimensions as a commercially available microplate, such that the bottom of the wells rest on the raised portion 56 and the perimeter of the microplate fits in the trench 58. The aluminum base plate 52 is designed such that the microplate is not adversely affected by the compression of the clamping plate 60 by the piston 28 when the pneumatic pressure unit 30 is actuated.

In some embodiments, the aluminum base plate 54 comprises a first heater 52. In some embodiments, the clamping plate 60 comprises a second heater 62. The first heater 52 and second heater 62, in some embodiments, comprise flexible silicone rubber heaters available from Omega.com. The first heater 52 and the second heater 62 can be controlled, in some embodiments, by a ¼ DIN six zone temperature controller with RS-232 communications and configuration software available by from Omega.com. It is to be understood that the heaters and heat control unit and the operation described herein provided are one embodiment which supplies heat to the automated cleansing unit 100. One of ordinary skill in the art will readily appreciate that other systems may be used to supply heat to the automated cleansing unit 100. The first heater 52 and the second heater 62 are used, in some embodiments, to stabilize the temperature of the sample and the skin mimic at room temperature ranging from about 20° C. to about 25° C. In other embodiments, the first heater 52 and the second heater 62 are used to stabilize the temperature of the sample and the skin mimic at a typical shower temperature ranging from about 38° C. to about 39° C.

Figure 5:
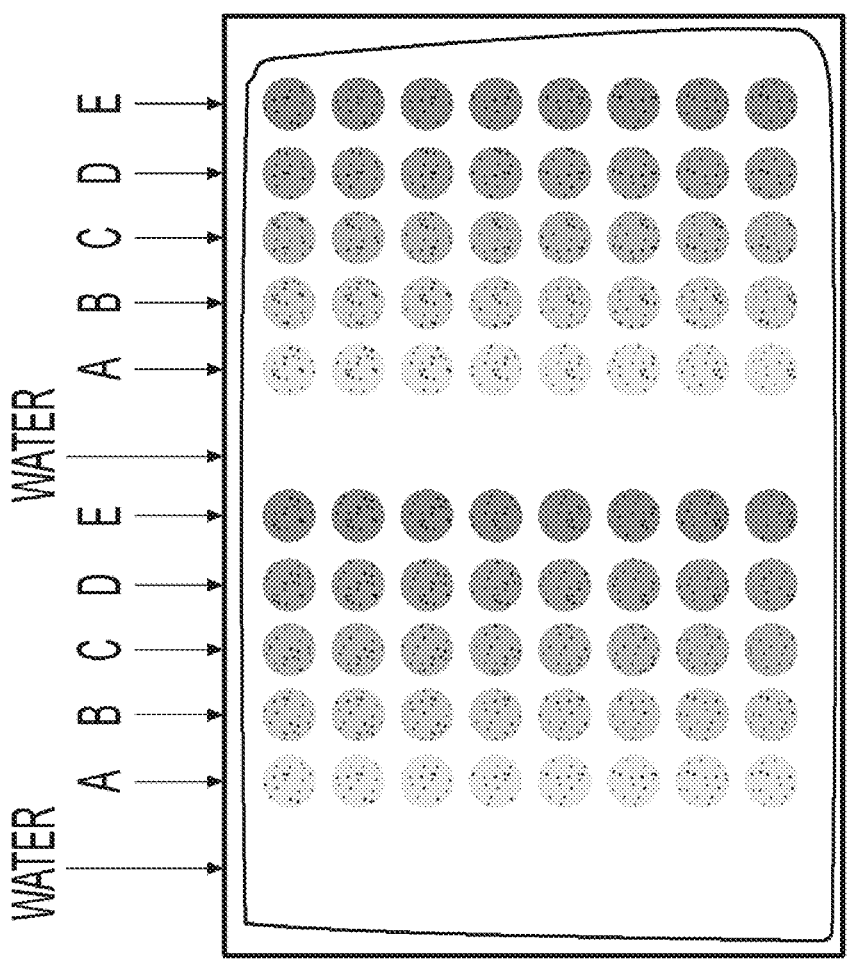
FIG. 5 is a photo of the skin mimic material after cleansing in the automated cleansing unit.

FIG. 5 is a photo of a skin mimic after the automated cleansing process with samples A B, C, D and E which comprised personal care compositions having various amounts of hydrophobic material. The control sample was water. Sample E shows whiter deposition areas than samples D, C, B, A and control. Thus, the personal care composition comprised within sample E has a better deposition profile than the personal care compositions comprised within samples D, C, B, A and control.

Test Methods

In-Vivo Deposition Method:

One method of evaluating deposition from personal care composition prototypes is a conventional in in-vivo deposition method which comprises an in-vivo forearm wash protocol on human test subjects (hereinafter referred to as "panelists") followed by measurement of deposited benefit agent on the skin of the panelists by a spectrophotometer. The spectrophotometer used in the in-vivo deposition method, is a FTIR. A suitable FTIR for this purpose is a FTIR with a 3-bounce diamond ATR, such as IdentifyIR® available from Smiths Detection. A computer is used in the in-vivo deposition method to control FTIR and collect data from the panelists and the FTIR. The computer is outfitted with a customized software package that has a macro for measuring deposition, such as the Customized version of GRAMS/32 software with deposition macro available from Thermo Scientific which stores spectra in Thermo Scientific SPC format. The in-vivo deposition method requires a source of running water having a controlled temperature in the range of 35-38° C. The method requires 1 ml syringes to hold the compositions of the control sample and the test sample. The in-vivo deposition method requires wash puffs (hereinafter referred to as "puffs") for applying the control sample and test sample onto the skin of the panelist. Two puffs are used per panelist, one for use with the control sample and another for use with the test sample.

Each panelist is asked to sign into the computer. The ATR of the FTIR is cleaned. The FTIR is verified with a background scan. The panelist is instructed to complete the in-vivo wash protocol for the left forearm. The in-vivo wash protocol is summarized below. After the panelist completes the in-vivo wash protocol for the left forearm, the panelist is instructed to place the washed portion of the left forearm on ATR. Eight scans are preformed on the left forearm by the FTIR. After the scan of the left forearm, the ATR is cleaned and verified with a background scan. Next, the panelist is instructed to complete the in-vivo wash protocol for the right forearm. After the panelist completes the in-vivo wash protocol for the right forearm, the panelist is instructed to place the washed portion of the right forearm on ATR. Eight scans are preformed on the right forearm by the FTIR.

The scans performed by the FTIR are the IR absorbance spectrum of the surface of the skin and the FTIR finds the maximum height of the C—H stretching band and normalizes it for arm contact/pressure to the Amide I band of the skin surface. The primary measure for the in-vivo deposition method is the percentage of deposition index which is the ratio of the deposition value measured for the control sample versus the deposition value measured for the test sample. The deposition value generated by the FTIR macro measures the absorbance of the benefit agents, CH stretching region, and normalizing to the pressure of the arm to the amide band. The deposition values measured are placed in a data file having the suffix (.csv) that is read by MICRSOFT® Excel and processed with an MICROSOFT® Excel macro that orders that data into the control sample and test sample columns. The individual ratios of control sample versus test sample are calculated, and the mean and standard deviation of those values are then calculated and reported. A T-test can be calculated to determine statistical significance. The deposition index can be converted to ug/cm$^2$ of deposition by comparing the deposition index to a calibration curve which is generated using known level of leave-on hydrocarbon materials on the forearm.

In-Vivo Wash Protocol:

The panelist instructed to obtain a sample comprising a personal care composition which is in a syringe (hereinafter referred to as "sample syringe") and a puff for the arm they are washing. The panelist is instructed to verify that the sample syringe number coordinates with their panelist number. The panelist is instructed to fluff the puff by pulling the nylon out from the center of the puff. The panelist is instructed to saturate the puff with running water for 5 seconds. The panelist is instructed to hold the puff in the hand of the forearm they are currently washing while wetting the forearm under running water for 5 seconds, letting water wash from the elbow to the wrist. After the forearm is wetted, the panelist is instructed to dispense the sample syringe into the hand opposite the forearm being washed and is warned not to apply the sample syringe directly to the arm from the sample syringe because it leads to uneven deposition of the sample. The panelist instructed to rub the sample onto the inw4×7s6tfner forearm from the elbow to the wrist in long, continuous, circular strokes for 5 seconds. The panelist is instructed to remove any excess sample sticking to the hand by rubbing the palm of the hand along the edge of the arm. Without re-wetting the puff, the panelist is instructed to lightly wash the inner forearm from the wrist to the elbow with the puff for 10 seconds in long, continuous, circular strokes, washing through the sample with each stroke. The panelist is told that the sample should look foamy on the forearm and if the sample looks streaky, the panelist told that too much pressure is being applied during the forearm washing. The panelist is instructed to leave the sample on the forearm for 15 seconds and then subsequently rinse the forearm with water from inner elbow to wrist for 15 seconds. Prior to the FTIR reading, the panelist is instructed to pat the forearm dry and air-dry for the forearm for 30 seconds. The panelist is asked to wash both forearms by the in-vivo wash protocol in the in-vivo deposition method.

EXAMPLES

Example of the In-Vitro Deposition Method of the Present Invention

A 96-well microplate is provided for containing the samples comprising the personal care composition in Table 3, below (hereinafter within the example referred to as "microplate"). Suitable 96-well microplates are commercially available from PerkinElmer and from VWR.com. For example, the SpectraPlate 96-MG from PerkinElmer has 8 rows and 12 columns with a well volume of 400 µl. The SpectraPlate 96-MG comprises the approximate dimensions of 14.6 mm in height, 127.8 mm in length and 85.5 mm in width. The SpectraPlate 96-MG has a well diameter of 7.15 mm, a well depth of 10.8 and a well to well spacing of 9.0 mm.

Eight bodies are loaded into each of the 96 wells of microplates to carefully to ensure the same number is loaded into each well. The bodies are spherical 2 mm stainless steel which comprise iron available from WLB Antriebeselemente Gmbh, Scarrastrasse 12, D-68307 Mannheim, Germany.

Before samples are prepared, the personal care compositions are prepared. Examples of personal care compositions were prepared according to Table 3 below:

TABLE 3

Personal Care Composition

| Ingredients: | Personal Care Composition # | | | | |
|---|---|---|---|---|---|
| I: Cleansing Phase Composition | | | | | |
| sodium trideceth sulfate, sulfated to >95% from ICONOL ™ TDA-3 tridecyl alcohol alkoxylate (BASF Corp.) | 1 | 2 | 3 | 4 | 5 |
| sodium lauryl sulfate (Procter & Gamble) | | | | | |
| sodium lauroamphoacetate (Cognis Corp.) | 8.5 | 8.5 | 8.5 | 8.5 | 8.5 |
| Guar hydroxypropyltrimonium chloride (N-HANCE ® from Aqualon) | 8.5 | 8.5 | 8.5 | 8.5 | 8.5 |
| polyethylene glycol (POLYOX ™ WSR-301 from Dow Chemical) | 5 | 5 | 5 | 5 | 5 |
| xanthan gum (KELTROL ® 1 1000 from CP Kelco) | 0.6 | 0.6 | 0.6 | 0.6 | 0.6 |
| sodium chloride | 0.15 | 0.15 | 0.15 | 0.15 | 0.15 |

TABLE 3-continued

Personal Care Composition

| Ingredients: | Personal Care Composition # | | | | |
|---|---|---|---|---|---|
| trideceth-3 (ICONOL ™ TDA-3I from BASF Corp.) | 0.22 | 0.22 | 0.22 | 0.22 | 0.22 |
| methyl chloro isothiazolinone and methyl isothiazolinone (KATHON ™ CG from Rohm & Haas) | 4.75 | 4.75 | 4.75 | 4.75 | 4.75 |
| Ethylenediaminetetraacetic acid (Dissolvine NA 2x from Akzo Nobel) | 2 | 2 | 2 | 2 | 2 |
| sodium benzoate | 0.033 | 0.033 | 0.033 | 0.033 | 0.033 |
| Perfume | 0.15 | 0.15 | 0.15 | 0.15 | 0.15 |
| citric acid, titrated to a pH of | 0.2 | 0.2 | 0.2 | 0.2 | 0.2 |
| Water | 1.8% | 1.8% | 1.8% | 1.8% | 1.8% |
|  | 5.7 ± 0.2 | 5.7 ± 0.2 | 5.7 ± 0.2 | 5.7 ± 0.2 | 5.7 ± 0.2 |
| II: Benefit Phase Composition | Q.S. | Q.S. | Q.S. | Q.S. | Q.S. |
| petrolatum (G2218 from Sonnerbonn) | | | | | |
| mineral oil (HYBROBRITE ® 1000 from Sonnerbonn) | | | | | |
| Titanium Oxide (RBTD-834-11S2 from Kobo Products) | 65.3 | 65.3 | 65.3 | 65.3 | 65.3 |

Amounts of each ingredient are approximate weight percentages by weight of the personal care composition
QS: indicates that this ingredient is used to bring the total to 100%

The preparation of personal care compositions 1-5 are summarized, as follows: In a first mixing vessel, citric acid and water were added at a 50:50 ratio, to form a citric acid solution. The trideceth-3 was added to a second mixing vessel. Both polyethylene glycol and xantham gum are added to the trideceth-3 in the second mixing vessel to form a polymer premix. The sodium chloride, sodium lauroamphoacetate, sodium lauryl sulfate and sodium trideceth sulfate were added into the polymer premix within the second mixing vessel. The pH of the composition within the second mixing vessel was adjusted using the citric acid solution until the pH reached 5.7±0.2. The perfume, preservatives, and minors were added to the composition within the second mixing vessel until homogeneous forming the cleaning phase composition.

In a third mixing vessel, petrolatum is added. Mineral oil is added to the petrolatum in the third mixing vessel and is heated to 88° C. The titanium dioxide is added to the mixture of petrolatum and mineral oil with mixing to form the benefit phase composition. The benefit phase composition was cooled to room temperature.

After the benefit phase composition was cooled the cleansing phase composition and the benefit phase composition is blended together at a ratio of 60:40 using a SpeedMixer™ (from FlackTek Inc.) at 2800 rpm for 1 min. Without further preparation, the personal care compositions 1-5 are subjected to the in-vivo deposition method, as described above.

Samples are prepared by combining a personal care composition and distilled water. For each personal care composition, 90±0.02 grams of distilled water is dispensed into a mixing vessel. The mixing vessel is secured to the base of a mixer, such as a table top mixer from IKA, the mixer blades are adjusted into the distilled water within the mixing vessel. A syringe is then zeroed on a balance. The syringe is filled with the designated personal care composition. The syringe is weighed and small amounts of the designated personal care composition are dispensed until 10 grams of the personal care composition remains in the syringe. The mixer is turned on at a speed of 500 rpm and the contents of the syringe are dispensed into the distilled water within the mixing vessel. The distilled water and the designated personal care composition are mixed for 2 minutes at 500 rpm forming the sample. The sample is withdrawn by syringe from the mixing vessel while the mixer is on at a speed of 300 rpm. The mixing and dispensing procedures are followed for mixing and dispensing for the control sample and the test samples 1-5. The control samples and test samples are dispensed in the specified wells of the microplate.

The skin mimic used in the in-vitro deposition methods is comprised of a molded bicomponent polyethylene substrate. The skin mimic is textured on one side with a pattern that resembles the texture of human skin. The textured side of the skin mimic is coated with 1,1,1-trimethyl-1-pentene that is plasma deposited. The skin mimic has a total surface energy of 32±1.0 (mJ/m$^2$), a zeta potential of (−) 27.4 (mV), a contact angle in water of 100±2.0.

The preparation of the skin mimic comprises the steps of preparing the metallic mold (a), forming the substrate of the skin mimic (b) and formation of the treated test mimic of the skin mimic. Providing the skin mimic comprises the steps of (a) providing the skin mimic preparing the metallic mold, (b) forming the substrate of the skin mimic and (c) formation of the treated test mimic of the skin mimic.

(a) Metallic Mold Preparation: A pattern resembling the texture of human forearm skin is formed from a photograph image of human forearm skin. The pattern is transferred to a clear sheet to form a mask. A DuPont™ MX series dry film photoresists is adhered to the metal sheet. The mask is placed on top of the metal sheet to form a metal/photoresist/mask. The composite of metal/photoresist/mask is exposed to an appropriate dose of UV light, using industry standard exposure tools. The mask is removed, the photoresist is developed and the metal sheet is etched using appropriate etching solutions, as described in standard textbooks on second level microelectronics packaging. For example, Donald Seraphim, Ronald Lasky and Che-Yu Li, Principles of Electronic Packaging (Mc-Graw Hill Inc.) (1989).

(b) Formation of the Substrate of the Skin Mimic: A 1:1 mixture of Skin-Flex SC-89

Stretch-paint and Skin-Flex SC-89 Thinner S4 SC-89 Thinner, both available from Burman Industries, (Van Nuys, Calif.) is poured into the prepared metallic mold and allowed to dry overnight. The amount of the mixture poured is adjusted according to the size of the mold, to yield a final substrate that is typically between 600 to 800 micrometers thick. After overnight drying, the substrate material is carefully peeled off of the metallic mold.

(c) Formation of the treated test region of skin mimic. The plasma deposition is performed in a plasma unit, between the two electrodes, by application of the continuous wave radiofrequency (hereinafter referred to as "RF") power. The effective plasma treatment area is approximately 40 cm by 20 cm. The plasma unit comprises a cylindrical vacuum chamber having a diameter of approximately 30.5 cm and a length of 61.0 cm. Vacuum is produced by means of a LEYBOLD™ PCS 25 vacuum pump. The RF energy is supplied from a PE 1000 ADVANCED ENERGY™ 40 KHz power supply, across a set of parallel aluminum electrodes in the vacuum chamber. The substrate is placed on a perforated aluminum sample tray in between parallel plate aluminum electrodes in the vacuum chamber and the vacuum chamber pressure is reduced to approximately 100 milliTorr (mTorr). The substrate to be plasma coated is substantially degassed by adding a mixture of argon and nitrogen gas into the vacuum chamber at flow rates of 20 sccm of argon and 10 sccm of nitrogen, (where "sccm" means standard cubic centimeter per minute) for about one hour. After the substrate is degassed for one hour, the vacuum chamber pressure is reduced to 10 mTorr and 25W of continuous wave RF power is applied for approximately 5 minutes while allowing the argon/nitrogen gas mixture to flow into the vacuum chamber at flow rates of 20 sccm of argon and 10 sccm of nitrogen. After 5 minutes, the release of gas is stopped and vacuum chamber is evacuated to the pressure of 10 mTorr. The 1,1,1-trimethyl-1-pentene coating material available from Aldrich is introduced into the vacuum chamber to a pressure of 100 mTorr at a flow rate selected is from about 10 sccm to 200 sccm depending the knowledge of or may be determined with limited experimentation by one of ordinary skill in the art. While the coating material is introduced into the vacuum chamber 25W of continuous wave RF power is applied for approximately 25 minutes while maintaining a vapor pressure of approximately 100-120 mTorr. The plasma deposition results in a polymeric coating of 1,1,1-trimethyl-1-pentene that is covalently bonded to the substrate. The exact times for plasma deposition will be within the knowledge or may be determined with limited experimentation by one of skill in the art. After 25 minutes, the power to the plasma unit is turned off and the flow of the coating material is stopped. The vacuum chamber is purged with about 20 sccm argon for about 30 min prior to the removal of the coated substrate. The plasma coated substrates are removed from the chamber the contact angle, the surface charge and the thickness of the coating layer is determined by video contact angle measurement system (VCA-2500 from ASM), zeta-potential measurement (Anton Parr Electrokinetic Analyzer, Model BI-EKA) and Atomic Force Microscopy (Q-Scope 250 from Quesant Corporation) methods. However, one of skill in the art will understand that a variety of coating materials, as described herein, may be used, the choice of which will be determined by the surface property of the keratinous tissue that one desires to reproduce.

After all of the wells of the microplate are filled with the samples and the pieces of skin are made and coated, the skin mimic is prepared for the in-vitro deposition method. Two pieces of skin mimic are prepared by cutting the skin mimic to fit on top of the openings of the wells of the microplate while wearing gloves. The two pieces of skin mimic pieces are numbered "1" and "2".

A base line spectral data was obtained by the spectrophotometer for both pieces of skin mimic, as described below.

Next, the pieces of skin mimics are arranged over the openings of the wells of the microplates. The pieces of skin mimic surface material are transferred to cover the openings of the wells of the each of the microplates to ensure that the textured and treated region of the skin mimic is facing the openings of the wells of the microplate. A lid is placed over each piece of the skin mimic and the associated microplate to form a lidded microplate.

In the exemplified embodiment, the step of causing at least one body to move wherein a portion of the sample is transferred to the treated test region of the skin mimic was accomplished by the automated cleansing unit, as shown in FIG. 2, FIG. 3 and FIG. 4 and described above. Prior to placing the lidded microplates into the microplate holders of automated cleansing unit, the air pressure control of the automated cleansing unit is turned on. The lidded microplates are placed into the microplate holders and pneumatic pressure unit is actuated such that the lidded microplates are held under 90 psi of pressure. The magnetic arms are actuated such that the arms sweep back and forth over the lidded microplates at a height of 2.65 cm above the microplate holders. The magnetic arms of the automated cleansing unit are turned on for 5 minutes at a speed of 6 sweeps per every 10 seconds.

After automated cleansing process, a spectra is obtained by the spectrophotometer for both pieces of skin mimic surface material.

Quantification by Spectroscopy:

For the comparison of in-vivo and in-vitro methods, shown in Table X, the Eye-one® IO Spectrophotometer from GretagMacbeth with Measure Tool Software (collectively hereinafter referred to as "spectrophotometer") and a computer associated with the spectrophotometer (hereinafter referred to as "computer") was utilized.

A base line spectral data was obtained by the spectrophotometer for both pieces of skin mimic. The reading surface of the spectrophotometer is cleaned prior to each reading. The reading surface of the spectrophotometer is black in order to provide adequate reflection. The first piece of skin mimic is placed on the reading surface with the textured and treated region of the skin mimic facing the spectrophotometer. Next, a piece of plastic having a plurality of holes which correspond in size to the openings of the microplate is placed over the textured and treated region of the skin mimic. A scan is then performed using the robot arm of the spectrophotometer. The baseline spectral data for the first piece of skin mimic is saved on a computer as the first baseline. The reading surface of the spectrophotometer is cleaned and the spectral data for the second piece of skin mimic surface is, as described for the first piece of skin mimic. The baseline spectral data for the second piece of skin mimic is saved on the computer as the second baseline.

After automated cleansing process, a spectra is obtained by the spectrophotometer for both pieces of skin mimic surface material. Prior to the spectral readings, two large 4000 ml beakers of 20° C. to 25° C. water are filled. The first piece of skin mimic is removed from the first microplate and submerged in the tap water within the first beaker five times. The second piece of skin mimic is removed from the second microplate and submerged within the second beaker five times. Both piece of skin mimic are blotted with paper towels and fumed in a drying hood for five minutes each. The completeness of rinsing step is judged visually by the lack of foam on the skin mimic and presence of defined circles of deposited material on the skin mimic. The reading surface of the spectrophotometer is cleaned. The first piece of skin mimic is placed on the reading surface with the textured and treated region of the first skin mimic facing the spectrophotometer. Next, a piece of plastic having a plurality of holes which correspond in size to the openings of the microplate is placed over the textured and treated region of the first skin mimic. The scan is then performed using the robot arm of the spectrophotometer. The baseline spectral data for the first piece of skin mimic material is saved for comparison with the first baseline. The reading surface of the spectrophotometer is cleaned and the spectral data for the second piece of skin mimic surface material is obtained by the aforesaid method. The baseline spectral data for the second skin mimic surface material is saved on a computer for comparison with the second baseline.

The spectrophotometer measures the L-a-b values for the skin mimic surface material before cleansing and after washing. The deposition values of the in-vitro method are reported as a Delta L value and are indicative of the deposition profile of each sample. The difference of the light intensity L or "Delta-L" is the L value after the cleansing—L value before cleansing (the baseline spectral data).

Solvent Extraction and Quantification by Chromatography:

Samples comprising personal care composition are first subjected to the in-vitro deposition method, as described above, without measuring the spectral data for the skin mimic before and after the automated cleansing process. The solvent extraction and quantification by chromatography, as described below is used for samples that comprised petrolatum and vitamin E. One of ordinary skill in the art will readily appreciate that other components of personal care compositions may be extracted and quantified using chromatography using solvents, internal standards, methods and techniques known to those of ordinary skill in the art.

(a) Extraction Step: After treatment in the automated cleansing unit, the skin mimic is removed from the microplate for analysis. Treated spots on skin mimic are cut out and placed into vials containing 2 ml of extraction solution (heptane with squalane @ 20 µg/ml as an internal standard). Vials are agitated on a vortex shaker at 1250 rpm for 10 minutes. One ml of extract is removed for vitamin E acetate analysis by High Performance Liquid Chromatography (hereinafter referred to as "HPLC"); the remainder is reserved for petrolatum analysis by gas chromatography (hereinafter referred to as "GC").

(b) Quantitative Analysis of Vitamin E Acetate Deposition: The liquid chromatography method is performed in normal-phase mode on an AGILENT® 1100 series HPLC with fluorescence detection available from Agilent Technologies and HewlettPackard. The separation is accomplished using a 10 minute isocratic run using 0.4% dioxane in hexanes as the mobile phase and a SUNFIRE™ silica column available from Waters Corporation. The elution of vitamin acetate is monitored on the fluorescence detector using excitation and emission wavelengths of 220 and 300 nm, respectively. The vitamin E acetate peaks generally elute at about 5.6 minutes in the run and are integrated without special requirements.

Calibration standards are generated to cover a linear range of concentrations from 200 part-per-billion to 20 part-per-million. Standards are made by step-wise dilution of a stock solution of vitamin E acetate. The system suitability is routinely monitored through the inclusion of a known concentration check sample that is included with the list of standards and must quantitate within 90-110% of its target value.

In the case of product deposition on skin mimic, blank samples of the skin mimic are also extracted and checked for the presence of interfering background signals.

(c) Quantitative Analysis of Petrolatum Deposition: The gas chromatography method is performed by 5:1 split injection onto a DB-1 high-temperature capillary column with flame ionization detection and hydrogen carrier gas. The separation is accomplished with an oven temperature program starting at 120° C. ramped at 35° C./minute to 375° C. held for 2 minutes. The 10-12 largest paraffin peaks, which elute from 2.4 min to 4.6 min, are grouped and used for quantification. The calibration is by internal standard, single point using a solution containing 4000 µg/ml petrolatum and 20 µg/ml squalane. The system suitability and interference checks are the same as in the HPLC method.

Quantification by X-Ray Fluorescence (Hereinafter Referred to as "XRF")

Samples comprising personal care composition are first subjected to the in-vitro deposition method, as described above, without measuring the spectral data for the skin mimic before and after the automated cleansing process. The quantification by XRF, as described below is used to quantitatively examine the surface of mimic for the presence of titanium dioxide ($TiO2$). $TiO2$ may be present as neat $TiO2$ or treated $TiO2$ in the form of interference pigment or surface modified pigment. In general, the X-ray source impinges on a region of the skin mimic, the X-ray source interacts with the element Ti and light is emitted from the skin mimic. This emitted light is a quantitative representation of the amount of Ti on the surface. One of ordinary skill in the art will readily appreciate that other components of personal care compositions may be quantified using XRF using solvents, internal standards, methods and techniques known to those of ordinary skill in the art.

After treatment, the mimic is removed for analysis. The XRF method uses a Philips PW2404 Wavelength Dispersive 4000 watt X-Ray Spectrometer (hereinafter referred to as "X-Ray Spectrometer"). The X-Ray Spectrometer does not have the capacity for the intact plate, so the treated portions of the skin mimic must be separated and examined groups of four wells at a time. The calibration of the instrument was accomplished by preparing standards of Titanium Dioxide (dispersed in Pentane or another suitable solvent), suspended in water with the use of SEPIGEL™ by SEPPIC. SEPIGEL™ is a gellant used to provide a more viscous solution to prevent migration of the standard from its desired location. Standards are prepared that comprise personal care composition comprising known levels of titanium dioxide. The standards are formulated to create the following levels of titanium dioxide in the personal care composition: 0%, 0.5%, 1%, 2%, 3%, and 4% of titanium dioxide. The standards are spiked onto 4-well slices of artificial skin mimic, recording the weight of the total amount of each standard. To analyze the standards and samples, it is necessary to use a liquid XRF sample cups to suspend the mimic between two pieces of film for the analysis. Suitable XRF sample cups are 30 mm liquid XRF cups commercially available by Chemplex. The XFR cup is prepared by laying one piece of 6 µm Mylar film, such that commercially available by Spex, over the bottom portion of the cup. The treated skin mimic is then placed treated side down on top of this film. A second layer of Mylar film is positioned over the mimic, and the second half of the cup is pressed into place, sandwiching the mimic in between the layers of the Mylar film. The preparation of the XRF cup is necessary to ensure that no other analyte but titanium dioxide is measured from the from a physical support of the X-ray Spectrometer. When the XRF cups are prepared, the XRF cups are placed into the stainless steel sample holders for analysis.

Using a 10 cc syringe, deliver a measured amount of product into a prepared XRF cup. The amount used can vary by instrument, as not all models allow for the same size of XRF cup. The analyst should use an amount that at least fills the cup ¾ of the way, then always use that volume for the other standards and all samples. Typical volumes are 5 cc to 10 cc, depending on the size of the XRF cup. Calibrate the instrument as per the instrument manual. The linearity of the resultant calibration curve must be at least 0.995. If not, check XRF cup to assure they are aligned, wrinkle-free, and do not contain air bubbles. Re-analyze any standards that are suspect. Any standards which fall lower than the curve could also imply that an air bubble in the syringe prevented an adequate amount of standard from being used in the measurement. In such a case, XRF cups should be prepared again and the analysis should be done again. It may be necessary to recreate standard products in case of manufacturing issues. If failure continues, check manual for troubleshooting tips and contact instrument technical support.

The XRF software associated X-ray Spectrometer chooses the instrument parameters, to optimize energy and resolution. The X-ray Spectrometer I have programmed the unit to use the largest diameter sample area (ie. collimator mask) so that the largest possible sample size is measured, allowing us to obtain lower levels of quantification. Standards are analyzed first to, build a calibration curve. Once the curve was in place, samples could be measured. Alternatively, samples can be measured at the same time, or even before the curve, then reprocessed once the curve is ready. To date the results obtained track as expected and match the Delta L trends seen in the 'whiteness' measurements.

The amount of titanium dioxide in the sample of personal care composition can be determined through the following calculation:

$$\frac{Kcps\text{TiO2(measured as Ti)} - \text{intercept}}{\text{Slope}}$$

The intercept and slope are determined from the calibration curve. Many X-Ray Spectrometer and the associated software will calculate this internally, as long as the correct concentration of standards are input prior to the analysis of the samples of the personal care composition.

Comparison of the Exemplary Embodiment of the In Vitro Deposition Method According to the Present Invention Versus the Conventional In-Vivo Deposition Method

TABLE 4

Comparison of samples by the in-vivo deposition methods and in-vitro deposition methods

| Example and Sample No. | In vitro deposition method (Delta L) | In vivo deposition method (ug/cm2 hydrocarbons) | Blending Ratio of cleansing phase:benefit phase |
|---|---|---|---|
| 1 | −0.18 | 48.4 | 90:10 |
| 2 | 4.87 | 76.7 | 80:20 |
| 3 | 10.61 | 97.1 | 70:30 |
| 4 | 14.77 | 109.5 | 60:40 |
| 5 | 17.84 | 118.4 | 50:50 |
| Test Duration: | 2 hours | <20 hours | — |
| Replications: | 32 | 17 | — |

Personal care compositions 1-5 were prepared as described above and assessed through the conventional in-vivo deposition method summarized in the Test Methods section above. Seventeen human panelists for were used for each exemplary composition 1-5. The total time to complete the in-vivo deposition method was greater than 20 hours.

Samples 1-5, were prepared as described in the exemplary embodiment of the in-vitro deposition method of the present invention, as described above. The total time to complete one test with all five test samples with 32 replicates for each sample is about 2 hours.

Figure 6:
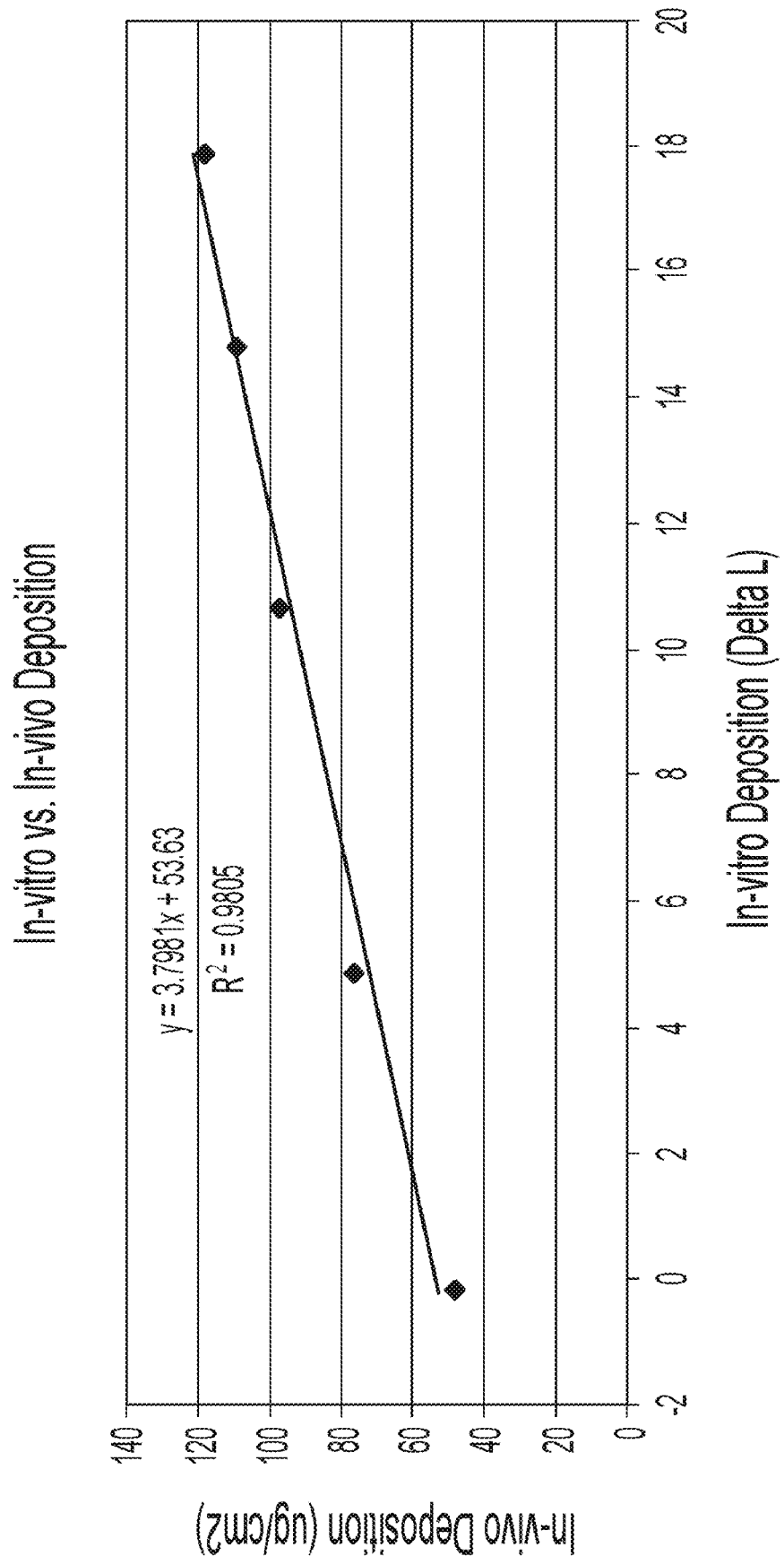
FIG. 6 is a graph correlating the results of the exemplary embodiment of the in vitro deposition method of the present invention and the results of the convention in vivo deposition method.

FIG. 6 is a graph correlating the results of the exemplary embodiment of the in vitro deposition method of the present invention and the results of the convention in vivo deposition method. The data illustrates that the results from the in-vivo deposition method and in-vitro deposition are highly correlated with a coefficient of determination, $R^2$ value of 0.9805 at a y=3.7981x+53.63. It is concluded that the in-vitro deposition method of the present invention provides researchers the capability to evaluate a large number samples at low sample volumes thereby dramatically accelerating the development of new and improved personal care compositions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An in-vitro deposition evaluation method comprising the steps of:
   a. providing a microplate comprising a base comprising a surface comprising a plurality of wells defined in said surface;
   b. providing at least one body in each of said plurality of wells; each body capable of movement within said well;
   c. providing a sample comprising a personal care composition;
   d. depositing a volume of said sample into each of said plurality of wells sufficient to submerge said at least one body;
   e. providing a skin mimic comprising a treated test region; wherein the skin mimic comprises:
      (1) a substrate comprising a polymer;
      (2) a coating layer comprising a plasma-deposited coating material selected from the group consisting of allyl amine, allyl alcohol, 1,1,1-trimethyl-1-pentene, 2,4,4-trimethyl-1-pentene, perfluoromethylcyclohexane monomer, and combinations thereof, wherein:
         i. said coating layer is stably affixed to said substrate to form a stable, coated surface, wherein said coated surface has a texture that mimics the topography of mammalian keratinous tissue; and ii. said coated surface demonstrates at least one physical property representative of mammalian keratinous tissue, selected from the group consisting of a total surface energy of from about 15 mJ/m$^2$ to about 50 mJ/m$^2$, a dispersive component of the surface energy of from about 15 mJ/m$^2$ to about 50 mJ/m$^2$, a polar component of the total surface energy of from about 1 mJ/m$^2$ to about 14 mJ/m$^2$, a zeta-potential at a pH of about 5.0 of from about −40 mV to about 30 mV, and combinations thereof; and f. contacting said treated test region to said surface of said microplate such that said treated test region is exposed to said sample and said body within each of said plurality of wells;

g. causing said at least one body to move wherein a portion of said sample is transferred to said treated test region of said skin mimic; and h. quantifying an amount of said sample that is transferred to said treated test region of said skin mimic.

2. The method of claim 1, wherein said body is comprised of a magnetic material.

3. The method claim of 1, wherein said microplate is selected from a 12-well microplate, a 24-well microplate, a 96-well microplate and a 384-well microplate.

4. The method of claim 1, wherein said causing step comprises the application of a force selected from magnetic force, electromagnetic force, electrical force, mechanical force and mixtures thereof.

5. The method of claim 1, wherein said quantifying step comprises the analytical method selected optical methods, spectroscopy, solvent extraction, biomedical techniques, chromatography, enzyme assays, physical measurements, radioactive labeling methods, immunochemical methods and mixtures thereof.

6. The method of claim 5, wherein said spectroscopy is selected from absorption spectroscopy, fluorescence spectroscopy, x-ray spectroscopy, flame, spectroscopy, visible spectroscopy, ultraviolet spectroscopy, Raman spectroscopy, nuclear magnetic resonance spectroscopy and photoemission spectroscopy.

7. The method of claim 1, wherein said personal care composition is selected from shampoo, conditioning shampoo, body wash, moisturizing body wash, shower gels, bar soaps, bath salts, bath beads, skin cleansers, cleansing milks, hair and body wash, in shower body moisturizer, pet shampoo, shaving creams and mixtures thereof.

8. An in-vitro deposition evaluation method comprising the steps of:

a. providing a microplate comprising a base comprising a surface comprising a plurality of wells defined in said surface;

b. providing at least one body comprising magnetic material in each of said plurality of wells; each body capable of movement within said well;

c. providing a sample comprising a personal care composition;

d. depositing a volume of said sample into each of said plurality of wells sufficient to submerge said at least one body;

e. providing a skin mimic comprising a treated test region wherein the skin mimic comprises:

(1) a substrate comprising a polymer;

(2) a coating layer comprising a plasma-deposited coating material selected from the group consisting of allyl amine, allyl alcohol, 1,1,1-trimethyl-1-pentene, 2,4,4-trimethyl-1-pentene, perfluoromethylcyclohexane monomer, and combinations thereof, wherein:

i. said coating layer is stably affixed to said substrate to form a stable, coated surface, wherein said coated surface has a texture that mimics the topography of mammalian keratinous tissue; and ii. said coated surface demonstrates at least one physical property representative of mammalian keratinous tissue, selected from the group consisting of a total surface energy of from about 15 mJ/m$^2$ to about 50 mJ/m$^2$, a dispersive component of the surface energy of from about 15 mJ/m$^2$ to about 50 mJ/m$^2$, a polar component of the total surface energy of from about 1 mJ/m$^2$ to about 14 mJ/m$^2$, a zeta-potential at a pH of about 5.0 of from about −40 mV to about 30 mV, and combinations thereof; and f. contacting said treated test region to said surface of said microplate such that said treated test region is exposed to said sample and said body within each of said plurality of wells;

g. causing said at least one body to move by the application of magnetic force onto said at least one body wherein a portion of said sample is transferred to said treated test region of said skin mimic; and h. quantifying an amount of said sample that is transferred to said treated test region of said skin mimic by spectroscopy.

9. The method of claim 8, wherein said sample comprises distilled water and said personal care composition in a ratio of from about 90:10 to about 70:30.

10. The method of claim 8, wherein said volume of said sample is less than about 4 ml.

11. The method of claim 8, wherein said volume of said sample is less than 320 µl.

12. The method of claim 8, wherein said quantifying step comprises infrared spectroscopy.

13. The method of claim 8, wherein said quantifying step comprises x-ray spectroscopy.

14. An assembly for in-vitro deposition comprising:

a. at least one microplate comprising a base comprising a surface comprising a plurality of wells defined in said surface;

b. at least one body in each of said plurality of wells; each body capable of movement within said well;

c. at least one piece of skin mimic comprising a treated test region; wherein said treated test region is in contact with said surface of said microplate such that said treated test region is exposed to said sample and said body within each of said plurality of wells; wherein the skin mimic comprises:

(1) a substrate comprising a polymer;

(2) a coating layer comprising a plasma-deposited coating material selected from the group consisting of allyl amine, allyl alcohol, 1,1,1-trimethyl-1-pentene, 2,4,4-trimethyl-1-pentene, perfluoromethylcyclohexane monomer, and combinations thereof, wherein:

i. said coating layer is stably affixed to said substrate to form a stable, coated surface, wherein said coated surface has a texture that mimics the topography of mammalian keratinous tissue; and ii. said coated surface demonstrates at least one physical property representative of mammalian keratinous tissue, selected from the group consisting of a total surface energy of from about 15 mJ/m² to about 50 mJ/m², a dispersive component of the surface energy of from about 15 mJ/m² to about 50 mJ/m², a polar component of the total surface energy of from about 1 mJ/m² to about 14 mJ/m², a zeta-potential at a pH of about 5.0 of from about −40 mV to about 30 mV, and combinations thereof; and d. a device for causing said at least one body to move wherein a portion of said sample is transferred to said treated test region of said skin mimic.

15. The assembly of claim 14, wherein said microplate comprises a 96 well microplate.

16. The assembly of claim 14, wherein said body comprises magnetic material.

17. The assembly of claim 14, wherein said device comprises at least one magnet.

18. The assembly of claim 17, wherein at least one magnet comprises a neodymium iron boron magnet.

* * * * *